United States Patent
Matyas et al.

(10) Patent No.: US 9,603,649 B2
(45) Date of Patent: Mar. 28, 2017

(54) INSTRUMENTS FOR USE IN DISASSEMBLING IMPLANTS

(71) Applicant: DEPUY IRELAND UNLIMITED COMPANY, Co Cork OT (IE)

(72) Inventors: Aaron J. Matyas, Fort Wayne, IN (US); Kyle D. Steffe, Warsaw, IN (US); Rebecca L. Chaney, Warsaw, IN (US); Tyler S. Hathaway, Auburn, IN (US); Michael A. Cook, Claypool, IN (US)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 795 days.

(21) Appl. No.: 13/837,465

(22) Filed: Mar. 15, 2013

(65) Prior Publication Data
US 2014/0276883 A1 Sep. 18, 2014

(51) Int. Cl.
*A61B 17/60* (2006.01)
*A61B 17/92* (2006.01)
*A61F 2/46* (2006.01)
*A61F 2/38* (2006.01)
*A61F 2/30* (2006.01)

(52) U.S. Cl.
CPC ............ *A61B 17/921* (2013.01); *A61F 2/461* (2013.01); *A61F 2/4637* (2013.01); *A61F 2/389* (2013.01); *A61F 2/3859* (2013.01); *A61F 2002/30332* (2013.01); *A61F 2002/30507* (2013.01); *A61F 2002/4627* (2013.01); *A61F 2002/4641* (2013.01)

(58) Field of Classification Search
CPC .......... A61F 2/46; A61F 2/461; A61F 2/4603; A61F 2/4637

USPC .......................................................... 606/104
See application file for complete search history.

(56) References Cited

U.S. PATENT DOCUMENTS

| 2,248,054 A | 7/1941 | Becker |
| 5,330,535 A | 7/1994 | Moser |
| 5,649,931 A * | 7/1997 | Bryant ............... A61B 17/8891 606/104 |

(Continued)

FOREIGN PATENT DOCUMENTS

| CN | 101095631 A | 1/2008 |
| CN | 101172062 A | 5/2008 |

(Continued)

OTHER PUBLICATIONS

Zimmer NexGen Lcck, Surgical Technique for use with LCCK 4-in-1 Instrument, 2009, 52 pages.

(Continued)

*Primary Examiner* — Matthew Lawson
(74) *Attorney, Agent, or Firm* — Barnes & Thornburg LLP

(57) ABSTRACT

An orthopedic surgical instrument for use in disassembling an orthopedic prosthesis includes a main component, a rod, and a spindle. The main component has a housing and an elongated body extending from the housing with a passageway is defined in the elongated body. The rod has an elongated shaft, with a greater length than the elongated body, extending from the head of the rod and configured to pass through the main component. The spindle threads into the housing to move the rod along a longitudinal axis.

7 Claims, 21 Drawing Sheets

(56) References Cited

U.S. PATENT DOCUMENTS

| | | | |
|---|---|---|---|
| 5,730,744 A * | 3/1998 | Justin | A61B 17/064 606/104 |
| 5,879,391 A | 3/1999 | Slamin | |
| 5,938,701 A | 8/1999 | Hiernard et al. | |
| 6,330,845 B1 * | 12/2001 | Meulink | A61B 17/8875 606/104 |
| 7,497,874 B1 | 3/2009 | Metzger et al. | |
| 8,518,050 B2 * | 8/2013 | McCleary | A61F 2/4637 606/99 |
| 8,556,912 B2 * | 10/2013 | Leisinger | A61F 2/4637 606/99 |
| 2004/0111861 A1 * | 6/2004 | Barrette | A61F 2/4637 29/426.5 |
| 2005/0107883 A1 | 5/2005 | Goodfried et al. | |
| 2005/0283251 A1 | 12/2005 | Coon et al. | |
| 2006/0030945 A1 | 2/2006 | Wright | |
| 2009/0005875 A1 | 1/2009 | Koenemann | |
| 2009/0149964 A1 | 6/2009 | May et al. | |
| 2012/0053698 A1 * | 3/2012 | Huff | A61F 2/4637 623/22.11 |

FOREIGN PATENT DOCUMENTS

| | | |
|---|---|---|
| CN | 101744675 A | 6/2010 |
| DE | 2810748 A1 | 11/1978 |
| DE | 4434806 A1 | 4/1996 |
| DE | 2011/085135 A1 | 4/2013 |
| EP | 0502815 A1 | 9/1992 |
| EP | 2425802 A1 | 3/2012 |
| FR | 1322212 A | 3/1963 |
| WO | 99/37253 A1 | 7/1999 |
| WO | 2007053905 A1 | 5/2007 |

OTHER PUBLICATIONS

DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Coordinate Ultra Revision Knee System, Surgical Technique, 1997, 24 pages.
P.F.C. Sigma Knee System, Revision, Surgical Technique, 2000, 66 pages.
Sigma Revision and M.B.T. Revision Tray, Surgical Technique, 2012, 84 pages.
S-Rom Noiles Rotating Hinge, Surgical Technique, 2012, 76 pages.
European Search Report for European Application No. 14159510.8, dated Jun. 4, 2014, 7 pages.
European Search Report for European Application No. 14159509.0, dated Jun. 3, 2014, 6 pages.
European Search Report and Written Opinion, European Application No. 14159518.1-1654, Jun. 16, 2014, 6 pages.
Search Report issued by the State Intellectual Property Office of People's Republic China in connection with Chinese Application No. 201410095313.X, dated Dec. 2, 2016, 3 pages.
First Office Action issued by the State Intellectual Property Office of People's Republic China in connection with Chinese Application No. 201410095313.X, dated Dec. 23, 2016, 3 pages.

* cited by examiner

INSTRUMENTS FOR USE IN DISASSEMBLING IMPLANTS

CROSS-REFERENCE

Cross reference is made to copending U.S. patent application Ser. No. 13/837,585 entitled "PROSTHETIC COMPONENTS AND METHODS FOR JOINT LINE ACCESS"; and copending U.S. patent application Ser. No. 13/837,778 entitled "PROSTHETIC COMPONENTS WITH SECONDARY RETENTION", each of which is assigned to the same assignee as the present application, each of which is filed concurrently herewith, and each of which is hereby incorporated by reference.

TECHNICAL FIELD

The present disclosure relates generally to an implantable orthopaedic prosthesis, and more particularly to an implantable knee prosthesis.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a knee replacement procedure, a tibial tray is implanted into the patient's tibia. A bearing is secured to the tibial tray. The condyle surfaces of a replacement femoral component bear against the tibial bearing.

Such a knee prosthesis may also include a number of elongated intramedullary stem components and optional prosthetic components (e.g., sleeves and/or adaptors) which are implanted in the patient's tibia and/or femur. To secure a stem component and/or other components to the patient's tibia and/or femur, the intramedullary canal of the patient's tibia and/or femur is first surgically prepared (e.g., reamed) such that the stem component and/or other components may be subsequently implanted therein. In some designs, the stem component is implanted in the patient's bone by use of cementless fixation. One type of such a design is known as a 'press fit' stem component.

Various orthopaedic surgical instruments are used throughout such an orthopaedic procedure. For example, bone saws and/or reamers may be use to surgically prepare a bone surface to accept an orthopaedic implant. Additionally, depending on the particularly implant, a variety of orthopaedic surgical instruments may be used to assembly, disassembly, and/or install the orthopaedic implant into the prepared bone.

SUMMARY

According to one aspect of the disclosure, an orthopaedic surgical instrument is disclosed. The orthopaedic surgical instrument includes a main component, a rod component, and a spindle component. The spindle component includes a housing and an elongated body extending from the housing. The housing and the elongated body define a longitudinal axis and a passageway is defined in the elongated body along the longitudinal axis. The rod component includes a head configured to be received in the housing of the main component and an elongated shaft extending from the head. The elongated shaft is configured to pass through the elongated body of the main component and has a length greater than a length of the elongated body of the main component. The spindle component includes a threaded body configured to thread into the housing to move the rod component along the longitudinal axis.

In some embodiments, the rod component may be selected from a plurality of rod components with each rod component of the plurality of rod components having an elongated shaft with a different length. An end of the elongated body of the main component opposite the housing may have a threaded outer surface. Additionally, the head of the rod component may have a diameter greater than a diameter of the passageway of the elongated body of the main component.

In some embodiments, the spindle component may include an aperture defined at an end of the threaded body, the aperture may be sized to fit the head of the rod component. Further, the diameter of the aperture may be less than a diameter of the spindle component. The spindle component may include a handle body opposite the threaded body configured to receive a handle component for threading the spindle component. An outer surface of the housing of the main component may be shaped to match a connection surface of a wrench component. Additionally, the outer surface may be shaped to match a connection surface of a hex wrench.

According to another aspect, a method for disassembling a femoral component assembly is disclosed. The method includes securing an end of a main component to a femoral component, advancing a rod in a first direction through the main component and into contact with a stem component secured to the femoral component and positioned in a bone of a patient, threading a spindle component into the main component to apply a force in the first direction to the rod, and continuing to thread the spindle component into the main component to increase the force applied in the first direction to disengage the femoral component from the stem component.

In some embodiments, the method may include removing a fastener securing the femoral component to the stem component from the femoral component assembly. Additionally, the method may include engaging a fastener with a driver positioned along a joint line, unthreading the fastener from the stem component using the driver, and removing the fastener from the femoral component assembly.

In some embodiments, the method may include removing a retention device from a threaded passageway of the stem post of the femoral component, such that the retention device is configured to prevent an end of the fastener from reentering the threaded passageway after being secured to the stem component. Removing the retention device may include driving a removal screw into the retention device. Additionally, the end of the main component to the femoral component may include threading an elongated body of the main component into a threaded passageway defined in the femoral component. Further, continuing to thread the spindle component may include continuing to thread the spindle component into the main component to increase the force applied in the first direction to move the femoral component in a second direction opposite the first direction.

According to another aspect, a method for disassembling an orthopaedic prosthesis assembly is disclosed. The method may include securing an end of a first surgical instrument to a first prosthetic component, advancing a rod in a first direction through the first prosthetic component and into contact with a second prosthetic component secured to the first prosthetic component, threading a second surgical instrument into the first surgical instrument to apply a force in the first direction to the rod, and continuing to thread the second surgical instrument into the first surgical instrument to increase the force applied in the first direction to the rod to disengage the first prosthetic component from the second prosthetic component.

In some embodiments, the method may include removing a fastener securing the first prosthetic component to the second prosthetic component and removing a retention device from a threaded passageway of the first prosthetic component, the retention device configured to prevent an end of the fastener from reentering the threaded passageway after being secured to the second prosthetic component. Further, securing the end of the first surgical instrument to the first prosthetic component may include threading an elongated body of the first surgical instrument into a threaded passageway defined in the first prosthetic component. Additionally, continuing to thread the second surgical instrument may include continuing to thread the second surgical instrument into the first surgical instrument to increase the force applied in the first direction to move the first prosthetic component in a second direction opposite the first direction.

According to another aspect of the disclosure, an implantable orthopaedic knee prosthesis assembly is disclosed. The implantable orthopaedic knee prosthesis assembly includes a femoral component configured to be implanted into a distal end of a femur of a patient, a stem component including a tapered post configured to be received in the tapered bore of the femoral component, a fastener, and a retention device. The femoral component includes a bearing surface having a medial condyle surface and a lateral condyle surface, a backside surface opposite the bearing surface, and a stem post extending superiorly away from the backside surface along an axis. The stem post has a proximal tapered bore, a distal passageway, and a threaded passageway connecting the proximal tapered bore and the distal passageway. The tapered post includes a bore formed therein extending proximally along the axis and a threaded aperture defined at a proximal end of the bore. The fastener includes a head configured to be received in the distal passageway and an elongated shaft having a proximal end configured to be positioned in the threaded aperture. Additionally, the retention device is configured to be received in the threaded passageway to prevent the proximal end of the fastener from entering the threaded passageway. Further, the head of the fastener has a diameter larger than a diameter of the threaded passageway and the elongated shaft has a diameter less than the diameter of the threaded passageway.

In some embodiments, the stem component may include an elongated body extending from the tapered post along the axis. The proximal end of the elongated shaft of the fastener may include a threaded portion to be threaded into the threaded aperture of the stem component. Additionally, a distance the fastener is configured to move with the retention device received in the threaded passageway may be a function of a length of the threaded portion. Further, the retention device may be composed of polymeric material.

According to another aspect, an orthopaedic prosthesis assembly includes a first prosthetic component, a second prosthetic component, a fastener, and a retention device. The first prosthetic component is configured to be implanted into a bone of a patient and includes a surface configured to contact the bone and a stem post extending away from the surface along an axis. The stem post has a tapered bore, a first passageway, and a threaded second passageway connecting the tapered bore and the first passageway. The second prosthetic component includes a tapered post received in the tapered bore of the first prosthetic component. Further, the tapered post has a bore formed therein extending along the axis and a threaded aperture defined at an end of the bore. The fastener includes a head received in the first passageway and an elongated body extending through the threaded second passageway along the axis and having an end positioned in the threaded aperture. Additionally, the retention device is received in the stem post to prevent the end of the fastener from entering the first passageway.

In some embodiments, the first prosthetic component may be a femoral component. In another embodiment, the first prosthetic component may be a tibial tray. The second prosthetic component may a stem component. Additionally, the head of the fastener may have a diameter greater than a diameter of the threaded second passageway and the elongated body of the fastener may have a diameter less than the diameter of the threaded second passageway. The end of the elongated body of the fastener may be threaded into the threaded aperture of the second prosthetic component.

In some embodiment, the elongated body of the fastener may be configured to pass through the retention device, and the retention device may be received in the threaded second passageway of the first prosthetic component. The retention device may be received in the first passageway. Additionally, the retention device may include polymeric material. Further, the retention device may include high molecular weight polyethylene.

According to another aspect, a method for assembling an implantable orthopaedic knee prosthesis assembly includes inserting a post of a stem component into a bore defined in a femoral component to secure the stem component to the femoral component, advancing an end of a fastener through a threaded passageway defined in the femoral component and into the post of the stem component, threading the end of the fastener into a threaded aperture defined in the stem component, and engaging a retention device with the femoral component to prevent the end of the fastener from reentering the threaded passageway after advancing the end of the fastener through the threaded passageway and into the post of the stem component.

In some embodiments, inserting the post of the stem component into the bore may include inserting a tapered post of a stem component into a tapered bore defined in a femoral component to secure the stem component to the femoral component. Additionally, the method may include inserting the assembled implantable orthopaedic knee prosthesis assembly into a prepared bone of a patient.

In some embodiments, engaging the retention device with the femoral component may include engaging a retention device with the threaded passageway of the femoral component to prevent the end of the fastener from reentering the threaded passageway after advancing the end of the fastener through the threaded passageway and into the post of the stem component. Additionally, engaging the retention device with the femoral component may include inserting a retention device into a passageway of the femoral component distal to the threaded passageway to prevent the end of the fastener from reentering the threaded passageway after advancing the end of the fastener through the threaded passageway and into the post of the stem component.

According to another aspect of this disclosure, a method for joint line assembly of an orthopaedic prosthesis assembly includes inserting a tapered post of a first prosthetic component into a tapered bore of a second prosthetic component along a longitudinal axis to secure the first prosthetic component to the second prosthetic component, advancing along the longitudinal axis a shaft of a fastener through a threaded passageway defined in the second prosthetic component and into the first prosthetic component such that the threaded passageway has a greater diameter than a diameter of the shaft, and threading an end of the shaft into a threaded aperture defined in the first prosthetic component.

In some embodiments, the first prosthetic component may be a stem component and the second prosthetic component may be a femoral component that may include a bearing surface having a medial condyle surface and a lateral condyle surface, a backside surface opposite the bearing surface, and a stem post extending superiorly away from the backside surface, the tapered bore being defined in the stem post. The second prosthetic component may be a femoral sleeve component including a plurality of step surfaces and the first prosthetic component may be a stem component including an elongated body extending from the tapered post.

In some embodiments, the method may include inserting a tapered stem post of a femoral component into a second tapered bore of the second prosthetic component to secure the femoral component to the second prosthetic component. The femoral component may include a bearing surface having a medial condyle surface and a lateral condyle surface, a backside surface opposite the bearing surface, and the tapered stem post extending superiorly away from the backside surface, and the first second prosthetic component may be a femoral sleeve component including a plurality of step surfaces and the first prosthetic component may be a stem component including an elongated body extending from the tapered post.

In some embodiments, the first prosthetic component may be a stem component including an elongated body extending from the tapered post and the second prosthetic component may be a tibial tray including a bearing surface configured to contact a bearing a backside surface opposite the bearing surface, and a stem post extending inferiorly away from the backside surface such that the tapered bore is defined in the stem post. Inserting the tapered post of the first prosthetic component into the tapered bore of the second prosthetic component may include securing the first prosthetic component to the second prosthetic component by a taper fit. Additionally, the first prosthetic component may be secured to the second prosthetic component by only the taper fit and the fastener. Further, the method may include advancing a retention device through the second prosthetic component along the longitudinal axis to engage the threaded passageway defined in the second prosthetic component.

According to another aspect, a method for joint line assembly of an orthopaedic prosthesis assembly may include inserting a tapered post of a stem component into a first tapered bore of a femoral sleeve component along a longitudinal axis to secure the stem component to the femoral sleeve component such that the first tapered bore is located at a first end of the femoral sleeve component, advancing along the longitudinal axis a shaft of a fastener through a threaded passageway defined in the femoral sleeve component and into the stem component such that the shaft has a first diameter and the threaded passageway has a second diameter greater than the first diameter, threading the end of the fastener into a threaded aperture defined in the stem component, and inserting a tapered stem post of a femoral component into a second tapered bore of the femoral sleeve component along the longitudinal axis to secure the femoral component to the femoral sleeve component such that the second tapered bore is located at a second end of the femoral sleeve component opposite the first end along the longitudinal axis.

In some embodiments, the stem component and the femoral sleeve component may be secured by only a taper fit between the stem component and the femoral component and the fastener. Additionally, the method may include inserting the stem component into a femur of a patient. Advancing the shaft of a fastener may include advancing a head of the fastener through a distal passageway defined in the femoral sleeve component distal to the threaded passageway, the head having a third diameter greater than the second diameter.

In some embodiment, advancing the end of the fastener through the threaded passageway may include advancing the end of the fastener through the threaded passageway defined in the femoral sleeve component prior to inserting the tapered stem post of the femoral component into the second tapered bore of the femoral sleeve component. The method may include advancing a retention device through the femoral sleeve component along the longitudinal axis to engage the threaded passageway defined in the femoral sleeve component.

According to another aspect of this disclosure, an orthopaedic prosthesis assembly is disclosed. The orthopaedic prosthesis assembly includes a first prosthetic component, a second prosthetic component, and a third prosthetic component. The first prosthetic component includes an outer surface, a surface positioned opposite the outer surface that is configured to contact a bone of a patient and a stem post extending from the surface along an axis. The second prosthetic component includes a first end secured to stem post of the first prosthetic component, a second end opposite the first end, and a tapered bore defined in the second end. The third prosthetic component includes a tapered post received in the tapered bore of the second prosthetic component. Further, the tapered post has a bore formed therein extending along the axis. Additionally, a passageway is defined in the orthopaedic knee prosthesis assembly along the axis from the outer surface of the first prosthetic component to an end of the bore of the third prosthetic component. A fastener extends along the axis is secured to the second prosthetic component and the third prosthetic component.

In some embodiments, each of the first prosthetic component, the second prosthetic component, and the third prosthetic component is devoid of an opening transverse to the axis. Additionally, the second prosthetic component may be a femoral sleeve component including a plurality of step surfaces and the third prosthetic component may be a stem component including an elongated body extending from the tapered post.

In some embodiments, the first prosthetic component may be a femoral component and may include the outer surface having a medial condyle surface and a lateral condyle surface, a backside surface opposite the bearing surface, and a tapered stem post extending superiorly away from the backside surface. In another embodiment, the first prosthetic component may be a tibial tray including the outer surface, which is configured to contact a bearing a backside surface opposite outer surface, and the stem post extending inferiorly away from the backside surface. In such an embodiment, the second prosthetic component may a tibial stem adaptor including a second tapered post defined at the first end and the third prosthetic component may be a stem component having an elongated body extending from the tapered post.

BRIEF DESCRIPTION OF THE DRAWINGS

The detailed description particularly refers to the following figures, in which.

DETAILED DESCRIPTION OF THE DRAWINGS

Figure 1:
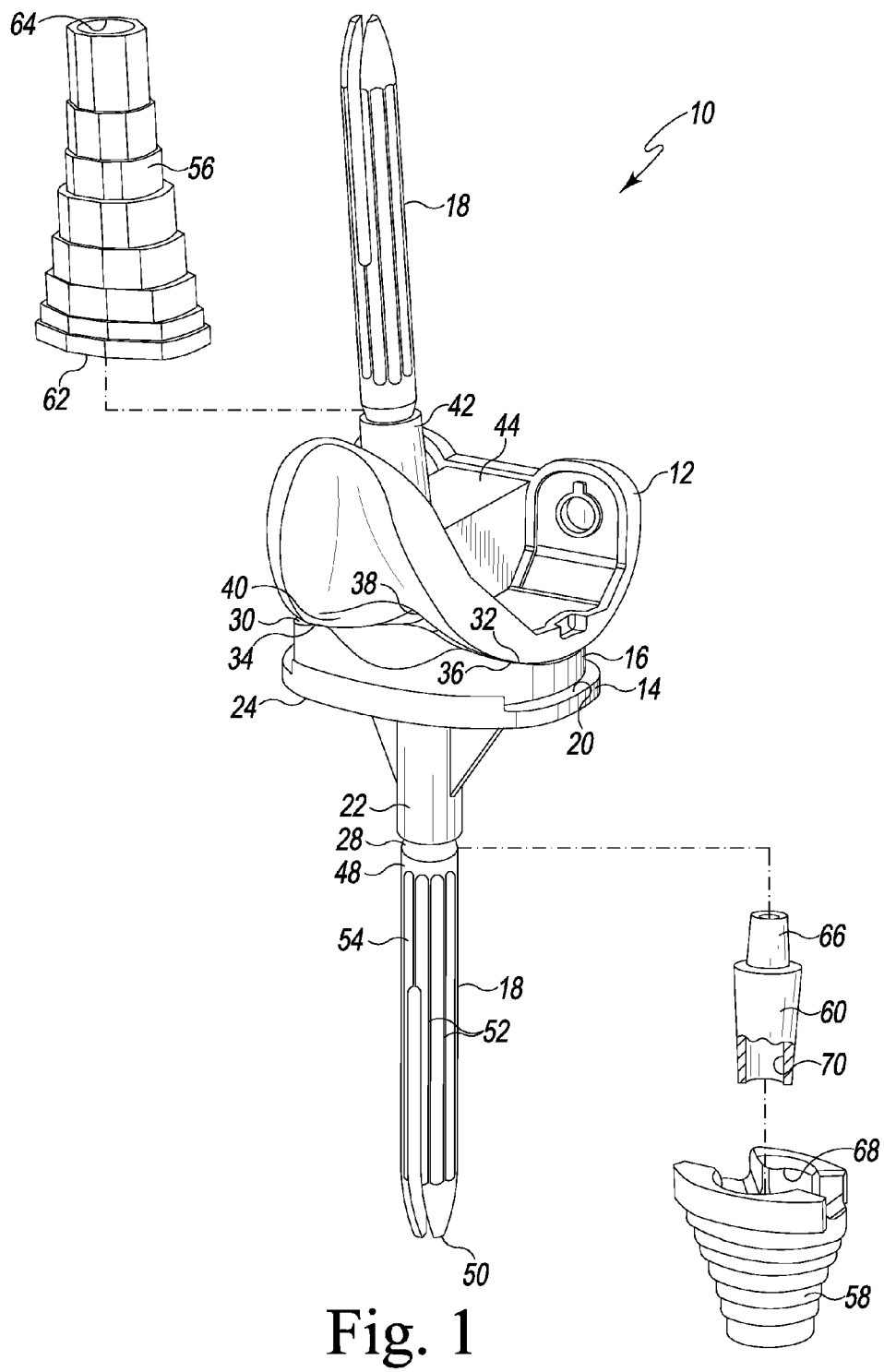
FIG. 1 is a perspective view of an implantable orthopaedic knee prosthesis assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown an implantable orthopaedic knee prosthesis assembly 10 for use in the performance of an orthopaedic knee replacement procedure. The knee prosthesis assembly 10 includes a femoral component 12, a tibial tray 14, and a bearing 16. The knee prosthesis assembly 10 also includes a stem component 18 secured to the femoral component 12 and a stem component 18 secured to the tibial tray 14.

The tibial tray 14 is configured to be implanted into a surgically-prepared end of a patient's proximal tibia (not shown). The tibial tray 14 includes a platform 20 having an elongated stem post 22 extending inferiorly away from its inferior surface 24. The elongated tibial stem post 22 is configured to receive the stem component 18. Specifically, the stem post 22 of the tibial tray 14 has a tapered bore 26 (see FIG. 5) formed therein into which a tapered post 28 of the stem component 18 may be advanced to taper lock the post 28 (and hence the stem component 18) and the tibial tray 14 to one another. In such a way, the stem component 18 may then be implanted into a surgically-prepared (e.g., reamed or broached) intramedullary canal of the patient's tibia. Further, as discussed in detail below, the tibial tray 14 and the stem component 18 each have threaded passages for use with a disassembly tool.

The bearing 16 is securable to the tibial tray 14. In particular, the bearing 16 may be snap-fit to the tibial tray 14. In such a way, the bearing 16 is fixed relative to the tibial tray 14 (i.e., it is not rotatable or moveable in the anterior/posterior or medial/lateral directions). Although, in other embodiments, the bearing 16 may be secured in a manner that allows it to rotate relative to the tibial tray 14.

The bearing 16 includes a lateral bearing surface 30 and a medial bearing surface 32. The bearing surfaces 30, 32 are configured to articulate with a lateral condyle surface 34 and a medial condyle surface 36, respectively, of the femoral component 12. Specifically, the femoral component 12 is configured to be implanted into a surgically-prepared distal end of the patient's femur (not shown), and is configured to emulate the configuration of the patient's natural femoral condyles. As such, the lateral condyle surface 34 and the medial condyle surface 36 are configured (e.g., curved) in a manner which mimics the condyles of the natural femur. The lateral condyle surface 34 and the medial condyle surface 36 are spaced apart from one another thereby defining an intercondylar notch 38 therebetween.

The condyle surfaces 34, 36 are formed in a bearing surface 40 of the femoral component 12. The femoral component 12 also includes an elongated stem post 42, extending superiorly away from its opposite backside surface 44. The elongated femoral stem post 42 is configured to receive the stem component 18. Specifically, the femoral component 12 has a tapered bore 46 formed therein into which a tapered post 28 of the stem component 18 may be advanced to taper lock the post 28 (and hence the stem component 18) and the femoral component 12 to one another (as shown in FIG. 1). In such a way, the stem component 18 may then be implanted into a surgically-prepared (e.g., reamed or broached) intramedullary canal of the patient's femur. Additionally, the femoral component 12 and the stem component 18 each have threaded passageways for use with the disassembly tool 208.

As shown in FIG. 1, each of the stem components 18 includes an elongated, generally cylindrical stem body 48. The tapered post 28 is positioned at a proximal end of the elongated stem body 48. The elongated stem body 48 extends distally away from the tapered post 28 and terminates at rounded distal end 50 that defines the inferior-most surface of the stem component 18 when it is secured to a tibial tray 14 or the superior-most surface of the stem component 18 when it is secured to a femoral component 12. As can be seen in FIG. 1, a number of elongated flutes 52 are formed in the outer annularly-shaped surface 54 of the stem body 48. The longitudinal axis of each of the flutes 52 is parallel to the longitudinal axis of the stem component 18 and hence is arranged in the superior/inferior direction.

The stem component 18 may be provided in a number of different configurations in order to fit the needs of a given patient's anatomy. In particular, the stem component 18 may be configured in various different lengths to conform to the patient's anatomy (e.g., a relatively long stem component 18 for use with a long femur or tibia, a relatively short stem component 18 for use with a short femur or tibia, etcetera). The stem component 18 may also be provided in varying body diameters to fit the needs of a given patient's anatomy. The body diameter of a given stem component 18 is the stem component's medial/lateral cross sectional width in the cylindrical midsection of the stem component's body (i.e., not at its tapered post or its distal tip). In other embodiments, the stem component 18 may have some other shape (e.g., non-cylindrical) and size. Likewise, the femoral component 12 and the tibial tray may 14 be provided in various different sizes to fit the needs of a given patient's anatomy.

As described below, the knee prosthesis assembly 10 may also include a number of optional components in various embodiments. For example, the knee prosthesis assembly 10 may include a femoral sleeve component 56, a tibial sleeve component 58, and a stem adaptor 60. The sleeve components 56, 58 may be used to facilitate implantation of the femoral component 12 and the tibial tray 14, respectively, in the presence of reduced bone quality in the patient's femur or tibia. The femoral sleeve component 56 is configured to be secured to the femoral component 12 so as to be positioned between the femoral component 12 and the stem component 18. In particular, the inferior end 62 of the femoral sleeve component 56 has a bore 180 formed therein that may be taper locked to the outer surface 182 of the femoral component's stem post 42 to lock the sleeve component 56 to the femoral component 12. The opposite, superior end of the femoral sleeve component 56 is configured to receive the stem components 18. Specifically, the superior end of the femoral sleeve component 56 has a tapered bore 64 formed therein into which a tapered post 28 of one of the stem components 18 may be advanced to taper lock the post 28 (and hence the stem component 18) and the femoral sleeve component 56 to one another.

The tibial sleeve component 58 may be embodied in a similar manner in which a bore formed in its superior end is taper locked to the stem post 22 of the tibial tray 14, with its opposite, inferior end having a tapered bore formed therein into which a tapered post 28 of one of the stem components 18 may be advanced to taper lock the post 28 (and hence the stem component 18) and the tibial sleeve component 58 to one another.

Alternatively, as shown in FIG. 1, the tibial sleeve component 56 may be used in conjunction with the stem adaptor 60. In such an embodiment, the stem adaptor 60 is used to secure both the stem components 18 and the tibial sleeve component 58 to the tibial tray 14. In particular, the stem adaptor 60 includes a tapered post 66 that is identical in shape and size to the tapered post 28 of each of the stem components 158. As such, the tapered post 66 of the stem adaptor 60 may be advanced into the tapered bore 26 formed in the tibial tray's stem post 22 to taper lock the post 22 (and hence the stem adaptor 60) and the tibial tray 14 to one another. The tibial sleeve component 58 is configured to be secured to the stem adaptor 60 so as to be positioned between the tibial tray 14 and the stem component 18. In particular, the tibial sleeve component 58 has a bore 68 formed therein that extends through its entire length and hence is open to both its superior end and its inferior end.

The tibial sleeve component 58 may be advanced over the stem adaptor 60 such that the tapered sidewalls forming the bore 68 of the tibial sleeve component 58 engage to the tapered outer surface of the stem adaptor 60 to taper lock the sleeve component 58 to the stem adaptor 60 to one another. As can be seen in FIG. 1, the inferior end of the stem adaptor 60 is configured to receive the stem components 18. Specifically, the inferior end of the stem adaptor 60 has a tapered bore 70 formed therein into which a tapered post 28 of one of the stem components 18 may be advanced to taper lock the post 28 (and hence the stem component 18) and the stem adaptor 60 to one another. Accordingly, it should be appreciated that each of the stem components 18 is configured to taper fit to any of the femoral component 12, the tibial tray 14, the femoral sleeve component 56, and the stem adaptor 60.

The components of the knee prosthesis assembly 10 that engage the natural bone, such as the femoral component 12, the tibial tray 14, the stem components 18, the sleeve components 56, 58, and the stem adaptor 60 may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic components may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The bearing 16 may be constructed with a material that allows for smooth articulation between the bearing and the femoral component 12, such as a polymeric material. One such polymeric material is polyethylene such as ultrahigh molecular weight polyethylene (UHMWPE).

Figure 2:
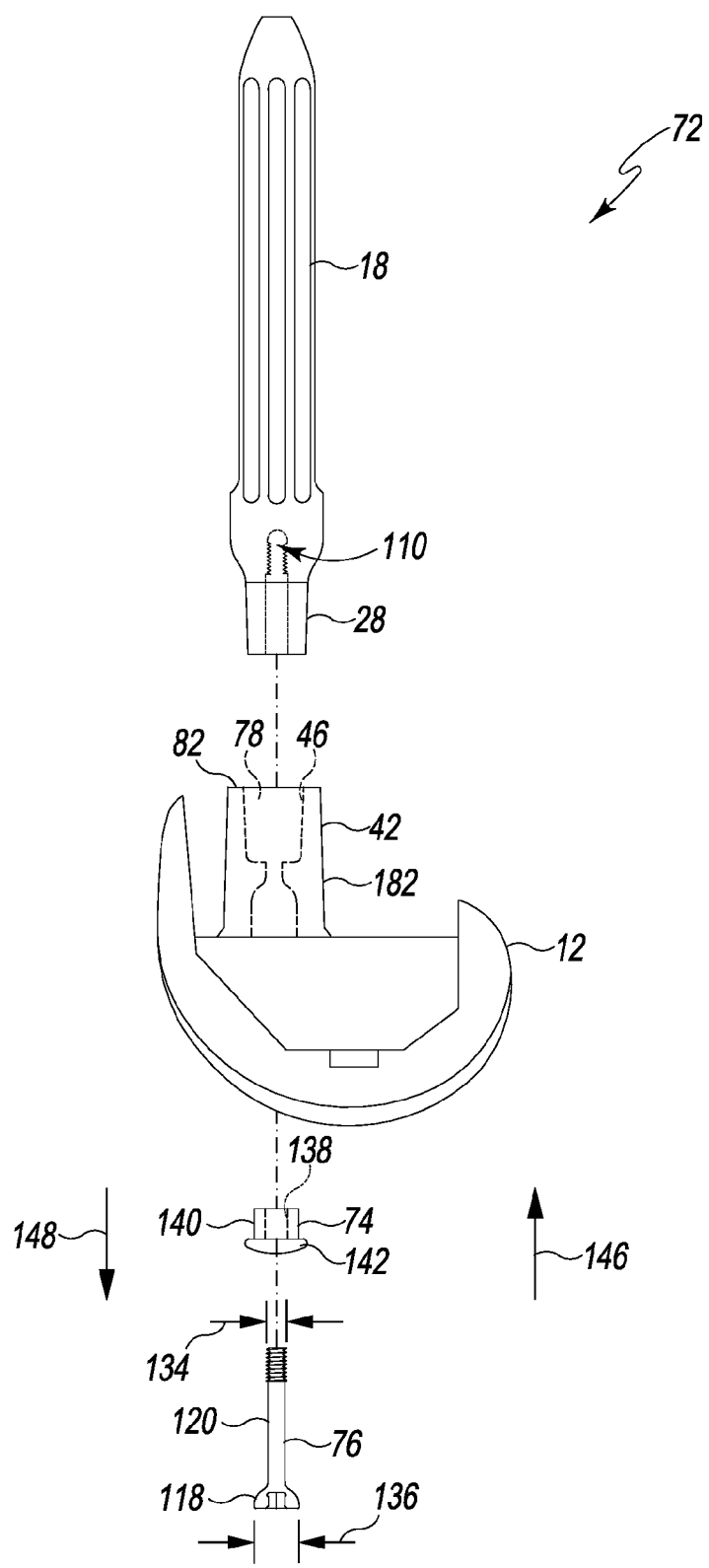
FIG. 2 is an exploded perspective view of a femoral component assembly of the implantable orthopaedic knee prosthesis assembly of FIG. 1.
Figure 3:
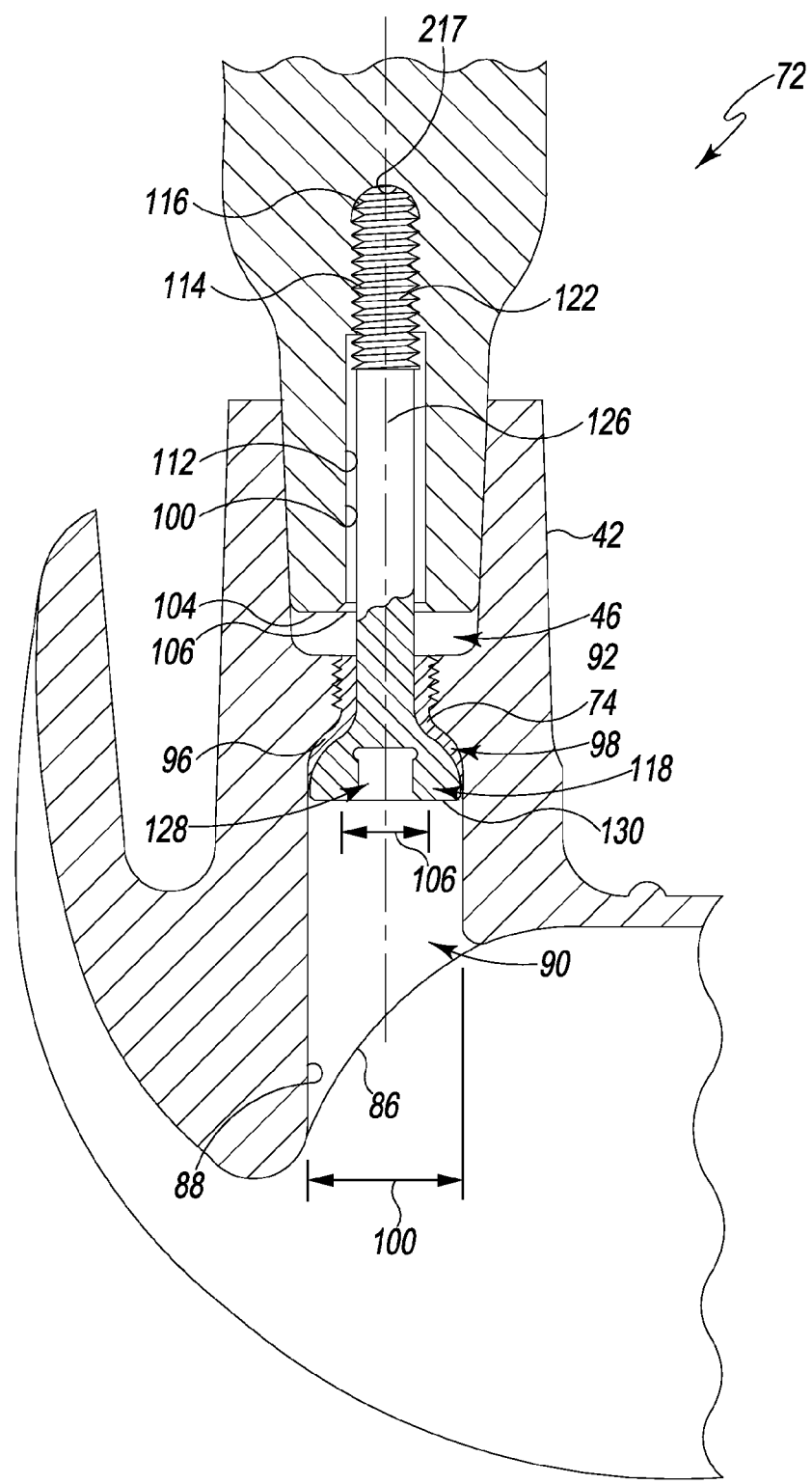
FIG. 3 is a cross sectional view of the femoral component assembly of FIG. 2.

Referring now to FIGS. 2-3, the femoral component assembly 72 includes the femoral component 12, a retention device 74, a fastener 76, and a stem component 18. As discussed above, the stem component 18 includes a tapered post 28 configured to be received in a tapered bore 46 formed in the stem post 42 of the femoral component 12 to taper lock the tapered post 28 (and hence the stem component 18) and the femoral component 12 to one another.

The stem post 42 of the femoral component 12 includes a passageway 78 extending from a distal end 80 to a proximal end 82 along an axis 84. As shown in FIG. 3, the distal end 80 of the passageway 78 defines an opening 86 from the intercondylar notch 38, and an inner wall 88 extends inwardly from the opening 86 to define the passageway 78. As shown, the passageway 78 includes the tapered bore 46 defined at the proximal end 82 of the passageway 78, a distal compartment 90 defined at the distal end 80 of the passageway 78, and a threaded passage 92 connecting the proximal tapered bore 46 and the distal compartment 90.

A plurality of internal threads 94 (see FIG. 7) are defined in the inner wall 88 within the threaded passage 92. As described below, the internal threads 94 are configured to engage external threads 254 of a disassembly tool 208. In that way, the disassembly tool 208 may be secured to the femoral component 12 during a disassembly procedure.

The inner wall 88 of the femoral component 12 includes an annular or cup-shaped connecting surface 96 defining a proximal end 98 of the distal compartment 90. As shown in FIG. 3, the distal compartment 90 has one diameter 100, and the threaded passage 92 has another diameter 102. Further, the diameter 100 of the distal compartment 90 is greater than the diameter 102 of the threaded passage 92. Accordingly, as shown in FIG. 3, the connecting surface 96 bridges the radial gap between the distal compartment 90 and the threaded passage 92.

The tapered post 28 of the stem component 18 includes a distal end 104 and an opening 106 defined in the distal end 104. An inner wall 108 extends inwardly from the opening 106 along the axis 84 to define an aperture 110 in the distal end 104 of the stem component 18. The inner wall 108 of the aperture 110 includes a substantially smooth unthreaded section 112 and a threaded section 114. As shown in FIG. 3, the threaded section 114 is defined at a proximal end 116 of the aperture 110 and includes a plurality of internal threads configured to engage corresponding threads of the fastener 76. As described in greater detail below, the proximal end 116 of the aperture 110 is defined by an engagement surface 217 configured to receive an end 274 of a rod component 214 during a disassembly procedure.

In the illustrative embodiment of FIGS. 2-3, the fastener 76 is a screw. It should be appreciated, however, that the fastener 76 may be any fastening device or component configured to extend through the femoral component 12 to the stem component 18 through the passageway 78. The fastener 76 includes a head 118 and an elongated shaft 120. As shown in FIG. 3, the elongated shaft 120 has a threaded section 122 at a base 124 of the fastener 76 opposite the head 118 and a substantially smooth unthreaded section 126 between the threaded section 122 and the head 118. The threaded section 122 of the fastener 76 includes a plurality of threads configured to engage the threaded section 114 of the aperture 110 of the stem component 18. The elongated shaft 120 is configured to pass through the distal compartment 90 and the threaded passage 92 of the femoral component 12.

A driver aperture 128 is defined in an upper surface 130 of the head 118 and is shaped to accept a surgical instrument driver 308. For example, the driver aperture 128 may be hex-shaped to accept a hex driver. Of course, the driver aperture 128 may be otherwise shaped to accept a surgical instrument driver head 316 of a different shape. The head 118 includes a lower surface 132 opposite the upper surface 132 configured to engage the connecting surface 96. As such, in some embodiments, the lower surface 132 may have a positive contour corresponding with a negative contour of the connecting surface 96. As shown in FIG. 3, the elongated shaft 120 of the fastener 76 has one diameter 134, and the head 118 has another diameter 136 that is greater than the diameter 134 of the elongated shaft 120.

The retention device 74 of the femoral component assembly 72 is configured to hold the fastener 76 in place once it has been secured to the stem component 18. In the illustrative embodiment of FIGS. 2-3, the retention device 74 is mushroom-shaped with a bore 138 extending along the axis 84. The bore 138 is configured to slide over the elongated shaft 120 of the fastener 76. It should be appreciated that, in some embodiments, the retention device 74 may be configured to slide along the unthreaded section 126 of the fastener 76 but not to slide along the threaded section 122 of the fastener 76.

The retention device 74 includes a cylindrical body 140 with a hood 142 extending radially from a distal end 144 of the cylindrical body 140. In some embodiments, the hood 142 may be a frustoconical body (or curved version thereof) extending from the cylindrical body 140. For example, the retention device 74 may be similar in shape to the retention device 74 described below in regard to FIG. 19 below with an optionally curved or rounded proximal end.

As shown in FIG. 3, the retention device 74 is shaped to tightly fit in the threaded passage 92 of the femoral component 12. In another embodiment, the retention device 74 may include only the cylindrical body 140 without the hood 142. Depending on the particular embodiment, the retention device 74 may also, for example, include a lock washer (e.g., a vinyl or polymeric washer) for use in retaining the fastener 76. The retention device 74 may be composed of any material suitable to be held in place by the threaded passage 92. In the illustrative embodiment, the retention device 74 may be composed of a polymeric material such a high molecular weight polyethylene.

In use, the tapered post 28 of the stem component 18 may be inserted into the femoral stem post 42 of the femoral component 12. A compressive load may be applied to the stem component 18 and the femoral component 12 to create a taper fit between the stem component 18 and the femoral component 12. In the illustrative embodiment, the taper fit acts as the primary fastener of the components 12, 18.

After the components 12, 18 are taper locked, the fastener 76 may be aligned with the retention device 74 along the axis 84. The threaded section 122 of the elongated shaft 120 of the fastener 76 may be inserted through the bore 138 of the retention device 74 to attach the fastener 76 to the retention device 74. The fastener 76 may then be aligned with the passageway 78 of the femoral component 12 along the axis 84, and the elongated shaft 120 of the fastener 76 may be advanced through the passageway 78 into the aperture 110 of the stem component 18. A surgical instrument driver may be used to thread the threaded section 122 of the fastener 76 into the threaded section 114 of the aperture 110 to advance the shaft 120 into contact with the engagement surface 217 at the end of the aperture 110.

As shown in FIG. 3, the elongated shaft 120 of the fastener 76 has a smaller diameter 134 than the diameter 102 of the threaded passage 92, whereas the head 118 has a greater diameter 136 than the threaded passage 92. Accordingly, while the elongated shaft 120 is configured to pass through the threaded passage 92 and the aperture 110, the head 118 is configured to rest in the distal compartment 90 but not pass through the threaded passage 92. As the retention device 74 is advanced into the threaded passage 92 (with the fastener 76) along the axis 84 in a first direction 146, the hood 142 of the retention device 74 is deformed toward a second direction 148 opposite the first direction 146 thereby creating a force sufficient to retain the fastener 76. As shown in FIG. 3, the hood 142 is compressed between the head 118 of the fastener 76 and the connecting surface 96 of the femoral component 12. In the illustrative embodiment, the fastener 76 and the retention device 74 act as a secondary fastener of the components 12, 18. In that way, the taper fit and the fastener 76 (with the retention device 74) act as dual or redundant attachment measures for the attached components (e.g., the femoral component 12 and the stem component 18).

Figure 4:
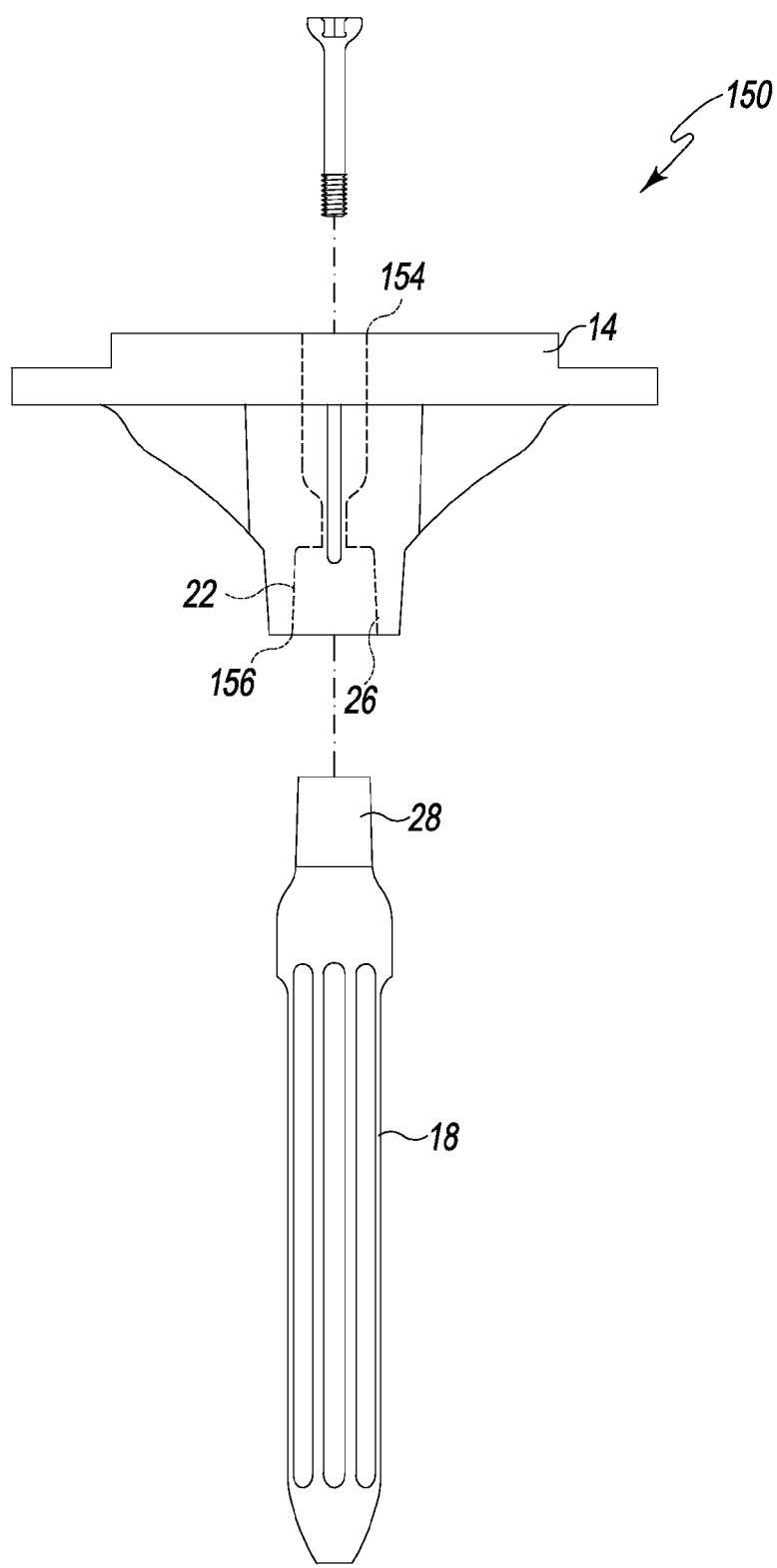
FIG. 4 is an exploded perspective view of a tibial component assembly of the implantable orthopaedic knee prosthesis assembly of FIG. 1.
Figure 5:
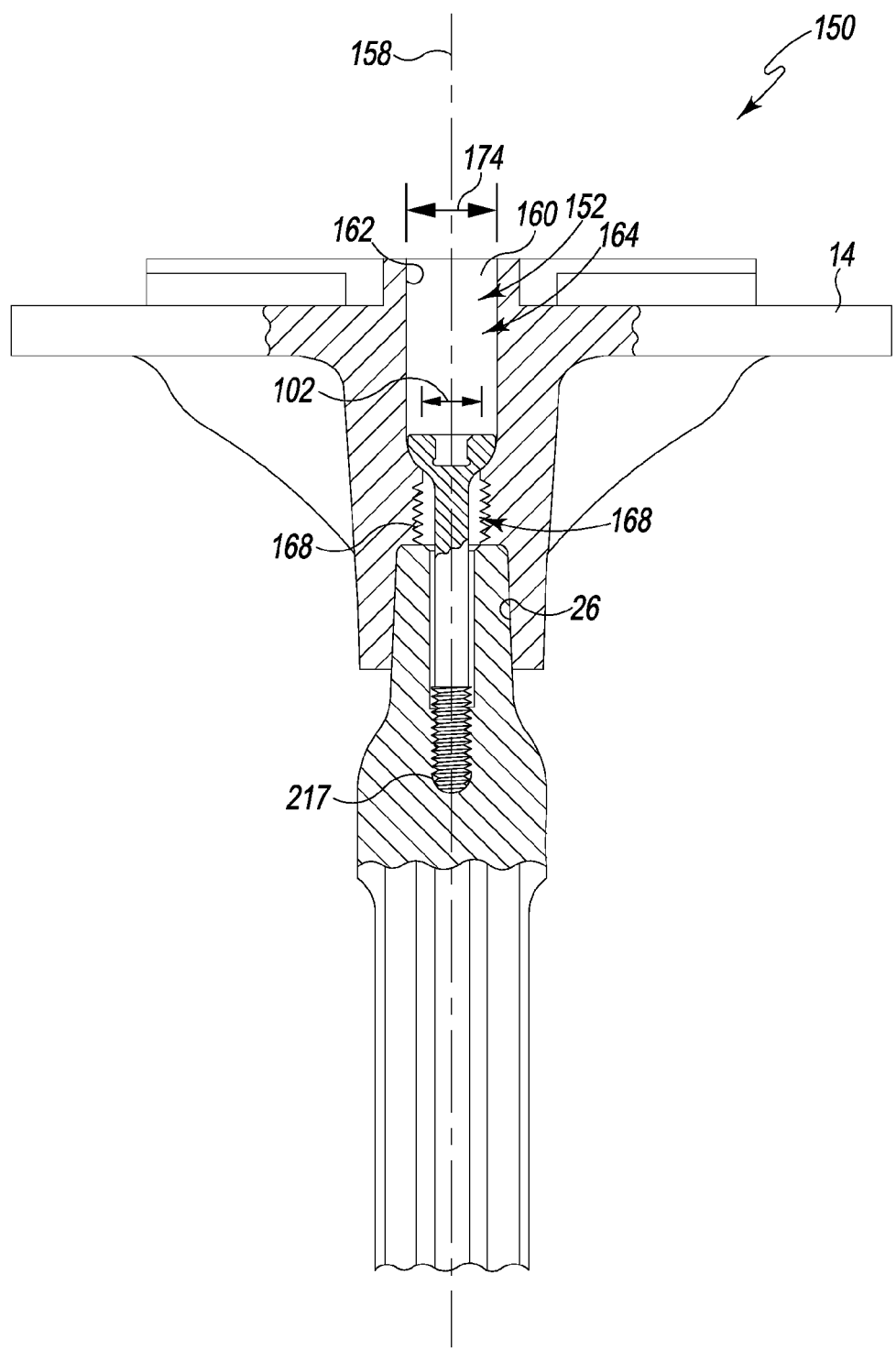
FIG. 5 is a cross sectional view of the tibial component assembly of FIG. 4.

Referring now to FIGS. 4-5, a tibial component assembly 150 includes the tibial tray 14, the fastener 76, and the stem component 18. As described above, the stem component 18 includes a tapered post 28 configured to be received in the tapered bore 26 formed in the tibial stem post 22 of the tibial tray 14 to taper lock the tapered post 28 (and hence the stem component 18) and the tibial tray 14 to one another.

The tibial stem post 22 of the tibial tray 14 includes a passageway 152 extending from a proximal end 154 to a distal end 156 along an axis 158. As shown in FIG. 5, the proximal end 154 of the passageway 152 defines an opening 160 in the platform 20, and an inner wall 162 extends inwardly from the opening 160 to define the passageway 152. As shown, the passageway 152 includes the tapered bore 26 defined at the distal end 156 of the passageway 152, a proximal compartment 164 defined at the proximal end 154 of the passageway 152, and a threaded passage 166 connecting the distal tapered bore 26 and the proximal compartment 164.

Similar to the femoral component 12, a plurality of internal threads 168 are defined in the inner wall 162 within the threaded passage 166. As described below, the internal threads 168 are configured to engage external threads 254 of a disassembly tool 208. In that way, the disassembly tool 208 may be secured to the tibial tray 14 during a disassembly procedure. Similar to the inner wall 88 of the femoral component 12, the inner wall 162 of the tibial tray 14 includes an annular or cup-shaped connecting surface 170 defining a distal end 172 of the proximal compartment 164. As shown in FIG. 5, the proximal compartment 164 has a diameter 174 that is greater than the diameter 102 of the threaded passage 166. Accordingly, the connecting surface 170 bridges the radial gap between the proximal compartment 164 and the threaded passage 166. In the illustrative embodiment, the proximal compartment 164 of the tibial tray 14 has the same diameter 100 as that of the distal compartment 90 of the femoral component 12.

In use, the tapered post 28 of the stem component 18 may be inserted into the femoral stem post 42 of the tibial tray 14. A compressive load may be applied to the stem component 18 and the tibial tray 14 to create a taper fit between the stem component 18 and the tibial tray 14. In the illustrative embodiment, the taper fit acts as the primary fastener of the components 14, 18.

After the components 14, 18 are taper locked, the fastener 76 may be aligned with the passageway 152 of the tibial tray 14, and the elongated shaft 120 of the fastener 76 may advanced through the passageway 152 into the aperture 110 of the stem component 18. A surgical instrument driver may be used to thread the threaded section 122 of the fastener 76 into the threaded section 114 of the aperture 110 to advance the shaft 120 into contact with the engagement surface 217 at the end of the aperture 110.

As shown in FIG. 5, the elongated shaft 120 of the fastener 76 has a smaller diameter 134 than the diameter 102 of the threaded passage 166, whereas the head 118 has a greater diameter 136 than the threaded passage 166. Accordingly, while the elongated shaft 120 is configured to pass through the threaded passage 166 and the aperture 110, the head 118 is configured to rest in the proximal compartment 164 but not pass through the threaded passage 166. In the illustrative embodiment, the fastener 76 acts as a secondary fastener of the components 14, 18. In that way, the taper fit and the fastener 76 (with the retention device 74) act as dual or redundant attachment measures for the attached components (e.g., the tibial tray 14 and the stem component 18).

It should be appreciated that in other embodiments a retention device similar to the retention device 74 of the femoral component assembly 72 may be used to secure the fastener 76 of the tibial component assembly 150. In such embodiments, the tibial component assembly 150 may be assembled in a manner similar to the assembly procedures described above with regard to assembling the femoral component assembly 72.

Figure 6:
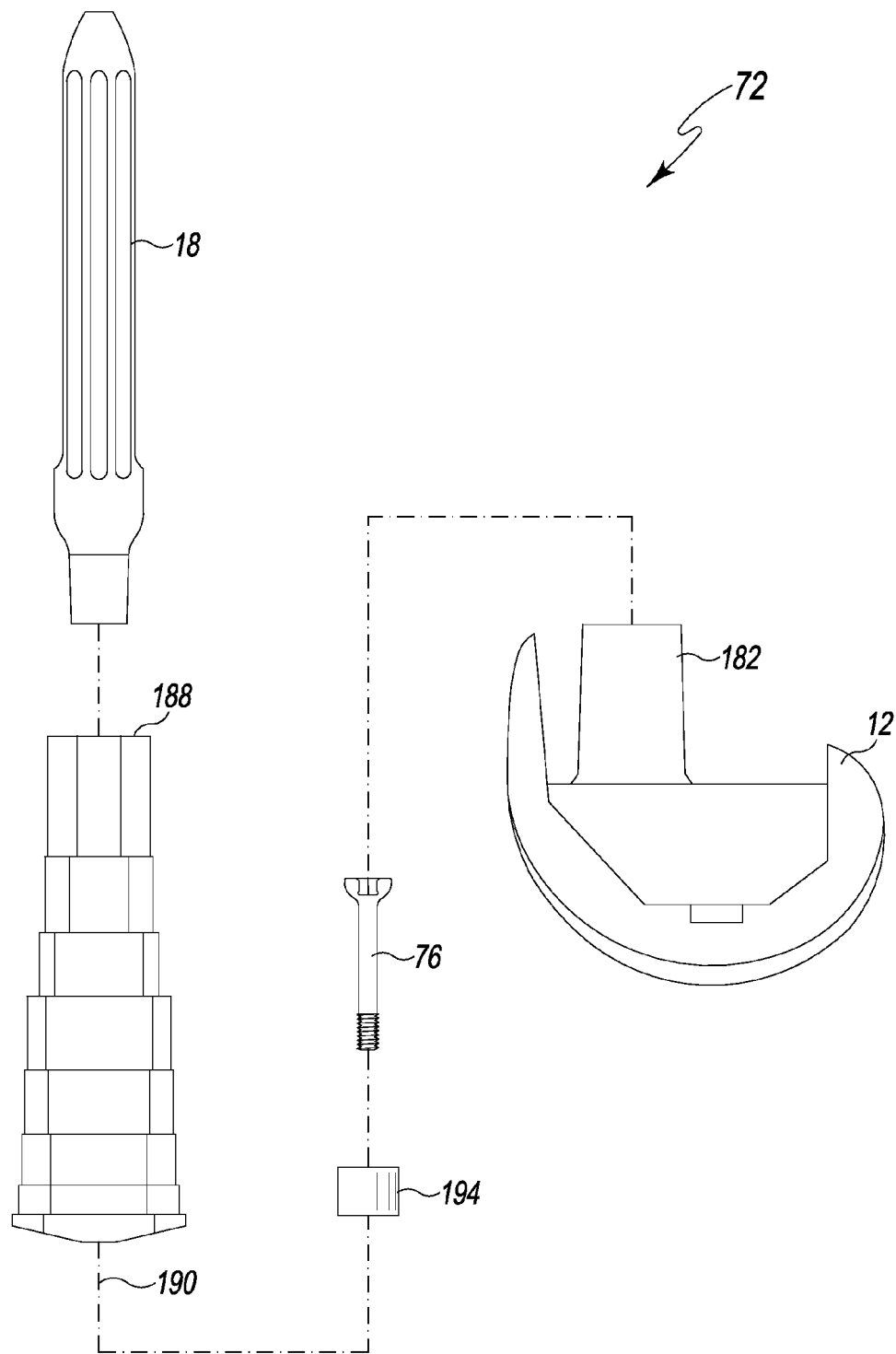
FIG. 6 is an exploded perspective view of a femoral component assembly including a femoral sleeve.
Figure 7:
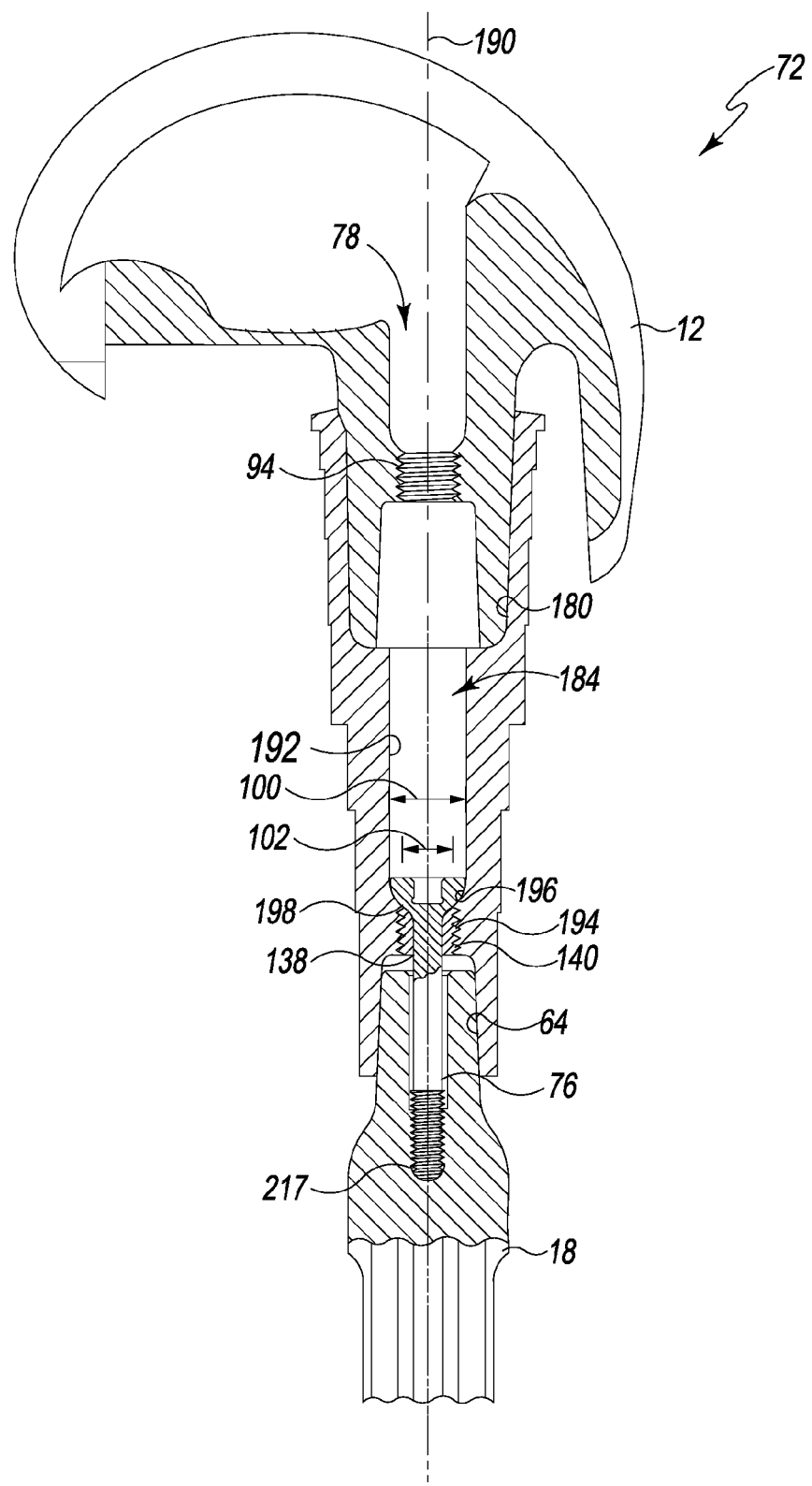
FIG. 7 is a cross sectional view of the femoral component assembly of FIG. 6.

Referring now to FIGS. 6-7, the femoral component assembly 72 may include the femoral sleeve component 56 as described above. The femoral sleeve component 56 includes a passageway 184 extending from a distal end 186 to a proximal end 188 along a longitudinal axis 190. As shown in FIG. 7, the passageway 184 includes a tapered bore 180 defined at the distal end 186 of the passageway 184 and a tapered bore 64 defined at the proximal end 188 of the passageway 184. The sleeve component 56 also includes a compartment 176 and a threaded passage 178 that connects the bores 64, 180.

As described above, the tapered bore 180 of the femoral sleeve component 56 may be taper locked to the outer surface 182 of the femoral component's stem post 42 to lock the sleeve component 56 to the femoral component 12. As shown in FIG. 7, the tapered bore 180 opens into the compartment 176 of the sleeve component 56. As such, when the sleeve component 56 is attached to the femoral component 12, the passageway 78 of the femoral component 12 opens into the compartment 176 (and hence the passageway 184) of the sleeve component 56.

The compartment 176 extends proximally from the tapered bore 180 to the threaded passage 178. As shown in FIG. 7, the femoral sleeve component 56 includes a plurality of internal threads that are defined in an inner wall 192 of the threaded passage 178. The threads, like the threads of the femoral component 12 and the tibial tray 14, are configured to engage external threads 254 of the disassembly tool 208 (e.g., during a disassembly procedure), as described in greater detail below.

Similar to the inner wall 88 of the femoral component 12, the inner wall 192 of the femoral sleeve component 56 also includes an annular or cup-shaped connecting surface 196 defining a proximal end 198 of the compartment 176. As shown in FIG. 7, the compartment 176 has a diameter 100 that is greater than the diameter 102 of the threaded passage 178. Accordingly, the connecting surface 170 bridges the radial gap between the proximal compartment 164 and the threaded passage 166. In some embodiments, the proximal compartment 164 of the tibial tray 14 has the same diameter 100 as that of the distal compartment 90 of the femoral component 12.

As described above, the femoral sleeve component 56 is also configured to receive the stem components 18. Specifically, the femoral sleeve component 56 has a tapered bore 64 formed therein into which a tapered post 28 of one of the stem components 18 may be advanced to taper lock the post 28 (and hence the stem component 18) and the femoral sleeve component 56 to one another. A fastener 76 may be used to secure the femoral component 12 to the stem component 18, as shown in FIG. 7.

The assembly 72 also includes a retention device 194 configured to hold the fastener 76 in place once it has been secured to the stem component 18. In the illustrative embodiment of FIGS. 2-3, the retention device 194 has a cylindrical body 140, and a bore 138 that is configured to slide over the elongated shaft 120 of the fastener 76. It should be appreciated that, in some embodiments, the retention device 194 may be configured to slide along the unthreaded section 126 of the fastener 76 but not to slide along the threaded section 122 of the fastener 76.

In use, the tapered post 28 of the stem component 18 may be inserted into the tapered bore 64 defined in the sleeve component 56. A compressive load may be applied to the stem component 18 and the femoral sleeve component 56 to create a taper fit between the stem component 18 and the sleeve component 56. In the illustrative embodiment, the taper fit acts as the primary fastener of the components 18, 56.

After the components 18, 56 are taper locked, the fastener 76 may be aligned with the retention device 194 along the axis 190. The threaded section 122 of the elongated shaft 120 of the fastener 76 may be inserted through the bore 138 of the retention device 194 to attach the fastener 76 to the retention device 194. The fastener 76 may then be aligned with the passageway 184 of the sleeve component 56 along the axis 84, and the elongated shaft 120 of the fastener 76 is advanced through the passageway 184 into the aperture 110 of the stem component 18. A surgical instrument driver may be used to thread the threaded section 122 of the fastener 76 into the threaded section 114 of the aperture 110 to advance the shaft 120 into contact with the engagement surface 217 at the end of the aperture 110. In the illustrative embodiment, the fastener 76 acts as a secondary fastener of the components 18, 56. In that way, the taper fit and the fastener 76 (with the retention device 194) act as dual or redundant attachment measures for the attached components (e.g., the sleeve component 56 and the stem component 18).

After the components 18, 56 are taper locked and secured together with the fastener 76, the tapered bore 180 of the femoral sleeve component 56 may be aligned with the femoral component's stem post 42 and the post 42 advanced into the tapered bore 180. A compressive load may be applied to the femoral component 12 and the femoral sleeve component 56 to create a taper fit between the femoral component 12 and the sleeve component 56 to secure the components 12, 56 together.

Figure 8:
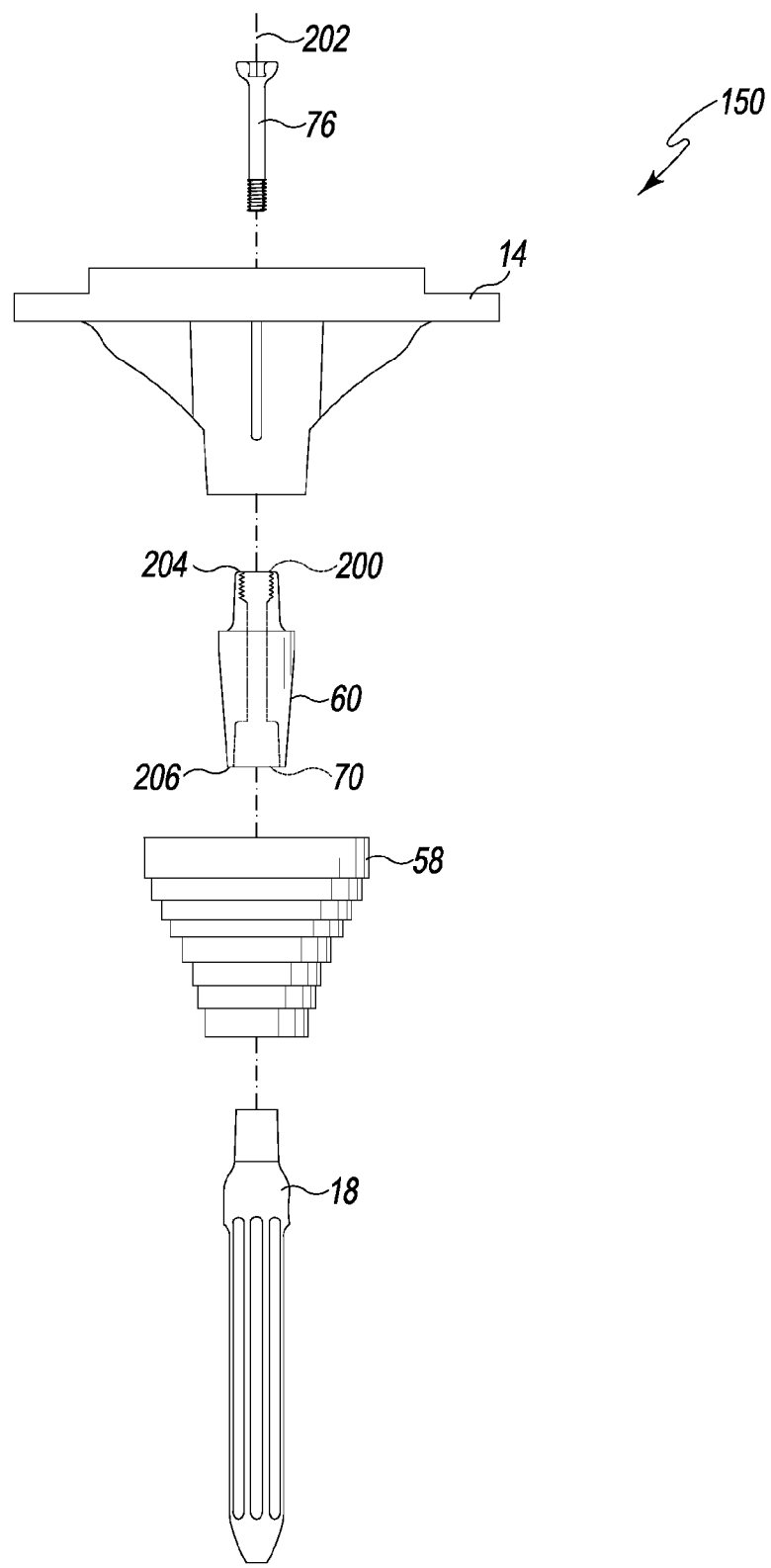
FIG. 8 is an exploded perspective view of a tibial component assembly including a tibial sleeve.

As shown in FIG. 8, the tibial sleeve component 58 may be used in conjunction with the stem adaptor 60 in the tibial component assembly 150. The stem adaptor 60 includes a passageway 200 defined along its longitudinal axis 202 from its superior end 204 to the tapered bore 70 defined at its inferior end 206. The passageway 200 includes a threaded passage 328 (see FIG. 17) at the stem adaptor's superior end 204 and a connecting passageway 330 (see FIG. 17) that connects the threaded passage 328 to the tapered bore 70. An inner wall (not shown) of the threaded passage 328 defines a plurality of threads 332 (see FIG. 17) configured to engage a disassembly tool 208, as described in greater detail below. During assembly, the fastener 76 may be advanced through the passageway 200 and engage the threaded section 114 of the aperture 110 of the stem component 18 to secure the stem adaptor 60 to the stem component 18. Although not shown, the threaded passage 166 of the tibial tray 14 adjoins the threaded passage 328 of the stem adaptor 60. Accordingly, in other embodiments, a retention device similar to retention devices 74, 194 may be used to secure the fastener 76 and may be positioned within the threaded passages 328, 166 of the tibial tray 14 and/or the stem adaptor 60.

Figures 9, 9A:
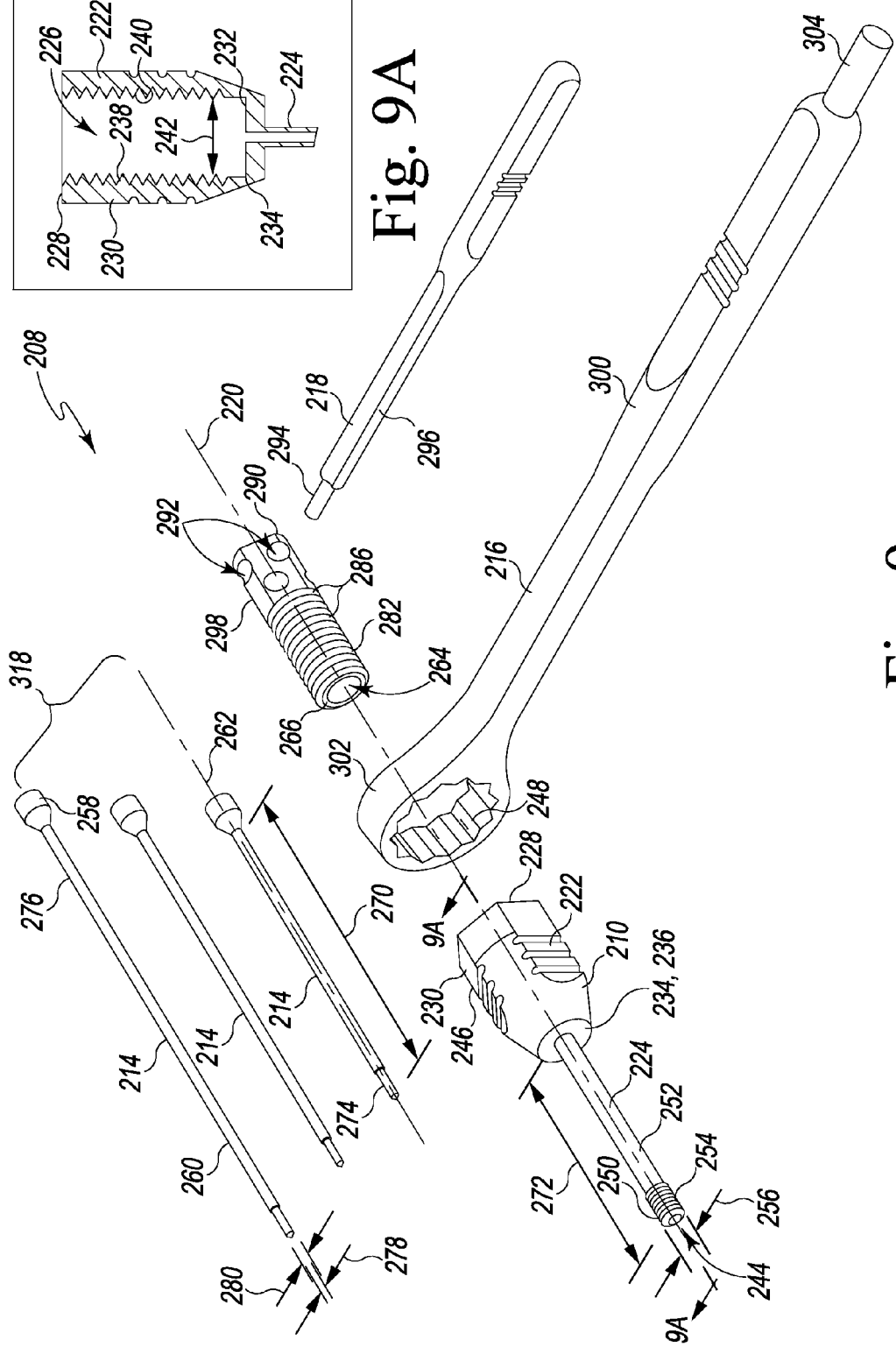
FIG. 9 is an exploded perspective view of a disassembly tool.
FIG. 9A is a fragmentary cross sectional view of a main component of the disassembly tool of FIG. 9 taken along the line 9A-9A in FIG. 9.

Referring now to FIG. 9, an exploded view of a disassembly tool 208 for use in disassembling an orthopaedic prosthetic component assembly 10 is shown. The disassembly tool 208 includes a main component 210, a spindle component 212, a rod component 214, a wrench component 216, and a handle component 218. As described below, the main component 210, the rod component 214, and the spindle component 212 may be assembled along a longitudinal axis 220. Each of the components of the disassembly tool 208 may be formed from a material capable of withstanding the mechanical stresses applied to those components as described below. In the illustrative embodiment, the components are formed from a metallic material, such as, for example, a stainless steel or a cobalt chromium alloy.

The main component 210 includes a housing 222 and an elongated body 224 extending inferiorly from the housing 222 along the longitudinal axis 220. As shown in FIG. 9A, the housing 222 has an aperture 226 formed therein extending from an opening 228 at its superior end 230 to an annular surface 232 defined at its inferior end 234. An inner wall 238 extends inferiorly from the opening 228 to define the aperture 226. A plurality of internal threads 240 are defined in the inner wall 238 within the aperture 226. In some embodiments, the plurality of internal threads 240 extend from the opening 228 to the annular surface 232, whereas, in other embodiments, the plurality of internal threads 240 may extend inferiorly only part of the way to the annular surface 232. As described below, the internal threads 240 are configured to engage the spindle component 212 of the disassembly tool 208 to force the rod component 214 inferiorly through a bore 244 defined in the elongated body 224.

As shown, a diameter 242 of the aperture 226 through the housing 222 is greater than a diameter 244 of the bore 244 of the elongated body 224 in the illustrative embodiment. Additionally, an outer surface 246 of the housing 222 is shaped to match a connection surface or socket 248 of the wrench component 216. That is, a cross section of a portion of the outer surface 246 of the housing 222 taken perpendicular to the longitudinal axis 220 corresponds to, fits, or otherwise matches a similar cross section of the socket 248 of the wrench component 216. For example, the outer surface 246 may be hex-shaped to be used with a hex wrench or square-shaped to be used with a square-shaped wrench.

As noted above, the elongated body 224 has a bore 244 formed therein that extends through its entire length and hence is open to both its superior end 236 and its inferior end 250. Additionally an outer surface 252 of the elongated body 224 at its inferior end 250 includes a plurality of threads 254. As discussed above, the threads 254 may be used to engage the threaded passages 92, 166, 178 of various orthopaedic prosthetic components during a disassembly procedure. As such, the elongated body 224 has an outer diameter 256 sized to fit through those threaded passages 92, 166, 178. For example, depending on the particular orthopaedic prosthetic assembly 10, the elongated body 224 is sized to fit through the distal compartment 90 of the femoral component 12, the proximal compartment 164 of the tibial tray 14, the tapered bore 46 of the femoral component's stem post 42, the compartment 176 of the femoral sleeve component 56, and the tapered bore 26 of the tibial tray's stem post 22 to engage the corresponding threaded passage.

Each rod component 214 of the disassembly tool 208 includes a head 258 and an elongated shaft 260 extending inferiorly from the head 258 along a longitudinal axis 262 of the rod component 214. The head 258 is sized to be received in the aperture 226 of the housing 222 of the main component 210 but not to pass through the elongated body 224 of the main component 210. As described below, in some embodiments, the head 258 is sized to fit an aperture 264 defined in an inferior end 266 of the spindle component 212. The elongated shaft 260 is configured to pass through the elongated body 224 of the main component 210 and has a length 270 greater than the length 272 of the elongated body 224.

In some embodiments, an inferior end 274 of the elongated shaft 260 of the rod component 214 may have a diameter 278 less than a diameter 280 of a superior end 276 of the elongated shaft 260 or be otherwise shaped to facilitate use of the rod component 214 with other orthopaedic prosthetic components or surgical instruments. For example, the inferior end 274 of the elongated shaft 260 may be shaped to easily fit through the threaded section 114 of the aperture 110 defined in the stem component 18 (e.g., to stably apply force to or "push off" the engagement surface 217 of the stem component 18 with the rod component 214 during a disassembly procedure). Alternatively, or additionally, the inferior end 274 of the elongated shaft 260 may be shaped to match the driver aperture 128 defined in the head 118 of the fastener 76 (e.g., to apply force to the fastener 76 with the rod component 214).

As shown in FIG. 9, the spindle component 212 includes a threaded body 282 extending superiorly from an inferior end 266 along the longitudinal axis 220. The outer surface 284 of the threaded body 282 includes a plurality of exterior threads 286 defined thereon, which are configured to engage the internal threads 240 of the housing 222 of the main component 210. As described above, in the illustrative embodiment, an aperture 264 is defined in the inferior end 266 of the spindle component 212 and may be sized to fit the head 258 of the rod component 214 (e.g., to stabilize the rod component 214 while applying a force to the rod component 214). However, in other embodiments, an aperture 264 may not be present.

The spindle component 212 also includes a handle body 288 opposite the threaded body 282 at a superior end 290 of the spindle component 212. The handle body 288 is configured to receive the handle component 218 for use in threading the spindle component 212 into the main component 210. As shown in FIG. 9, the handle body 288 may include a plurality of slots 292 through which an end 294 of the handle component 218 may be inserted during operation of the disassembly tool 208. In another embodiment, the handle body 288 may be shaped to otherwise secure the handle component 218. For example, the handle body 288 may have an outer surface 298 shaped to match the socket 248 another wrench component 216 in a manner similar to the outer surface 246 of the housing 222 of the main component 210.

The handle component 218 may include an elongated body 296 with the end 294 sized to fit through one or more of the slots 292 defined in the handle body 288 of the spindle component 212. As discussed above, in another embodiment, the handle component 218 may have a socket 248 to match a corresponding outer surface 298 of the handle body 288 of the spindle component 212 (i.e., the handle component 218 may be another wrench component 216). The wrench component 216 includes an elongated body 300 with a first end 302 and a second end 304 opposite the first end 302. As shown, the socket 248 is defined at the first end 302 of the elongated body 300 and configured to match the outer surface 246 of the housing 222 of the main component 210. Additionally, the second end 304 may be shaped to accept a leveraging tool (not shown) or some other tool used during a disassembly procedure. It should be appreciated that the handle component 218 and the wrench component 216 may be shaped as shown in FIG. 9 or configured in some other way suitable for performing the functions described herein.

As shown in FIGS. 10-15, an orthopaedic surgical procedure to disassemble the femoral component assembly 72 using the disassembly tool 208. While the procedure is described in reference the assembly 72, the procedure and the tool 208 may be used to disassemble the other orthopaedic component assemblies. It should be appreciated that the methods described herein permit a surgeon to disassemble (and assemble) orthopaedic prosthetic component assemblies from the joint line. In other words, the orthopaedic component assemblies may be disassembled from an end of the relevant long bone. For example, in the case of a femoral component assembly 72, the components, the fastener, and the retention device may be accessed from the distal end of the femur such that the surgeon may remove the fastener and the retention device and detach the femoral component without removing the stem component. In the case of the tibial component assembly 150 without a tibial sleeve component 58 or stem adaptor 60, the components and the fastener may be accessed from the proximal end of the tibia such that the surgeon may remove the fastener and detach the tibia component without removing the stem component. In the case of a tibial component assembly 150 with a tibial sleeve component and a stem adaptor 60, the components and the fastener may be accessed from the proximal end of the tibia such that the surgeon may remove the fastener and detach the tibia component and the stem adaptor 60 without removing the stem component and the tibial sleeve component 58.

Figure 10:
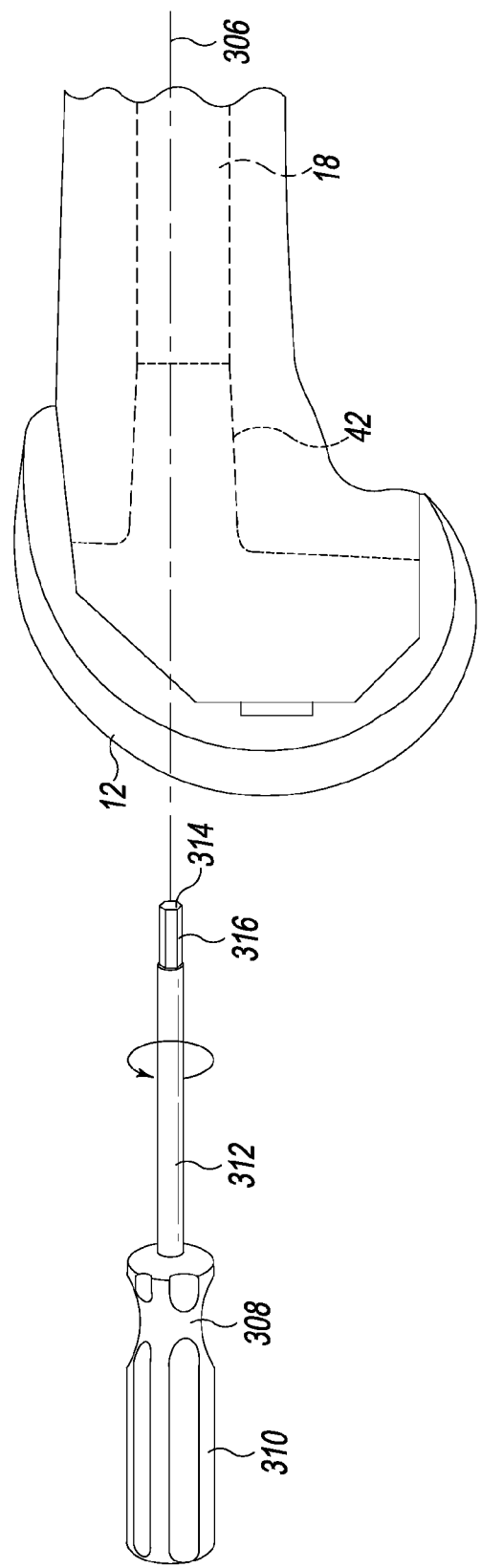
FIGS. 10-15 show the disassembly tool of FIG. 9 used in an orthopaedic surgical procedure with the femoral component assembly of FIGS. 1-3.
Figure 11:
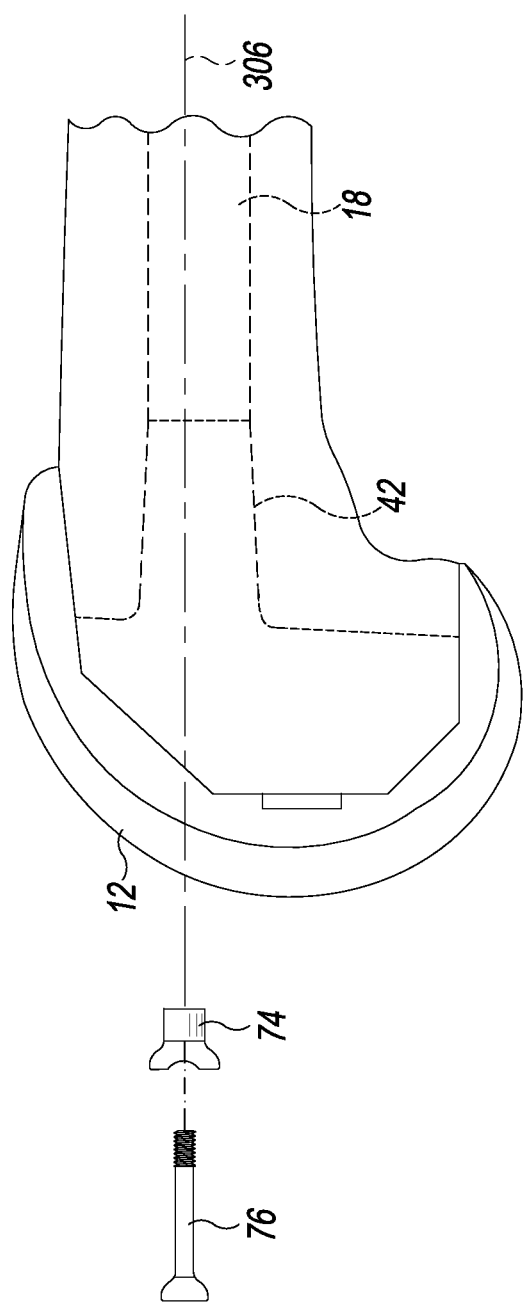

Referring now to FIGS. 10-11, the surgeon may remove the fastener 76 from the femoral component assembly 72 using a surgical instrument driver 308. As discussed above, the fastener 76 may secure the femoral component 12 to the stem component 18 in addition to the taper fit between those components. In the illustrative embodiment, the driver 308 includes a handle 310 and an elongated shaft 312 extending from the handle 310. As shown, a driver head 316 is defined at an end 314 of the elongated shaft 312 opposite the handle 310. It should be appreciated that the surgeon may use a driver 308 with a head 316 having a shape matching that of the driver aperture 128 of the fastener 76. For example, if the fastener 76 is a hex screw, a hex driver may be used to remove the fastener 76 from the femoral component assembly 72. In some embodiments, removing the fastener 76 involves unscrewing it from the stem component 18 and extracting it from the passageway 78 of the femoral component assembly 72.

Figure 12:
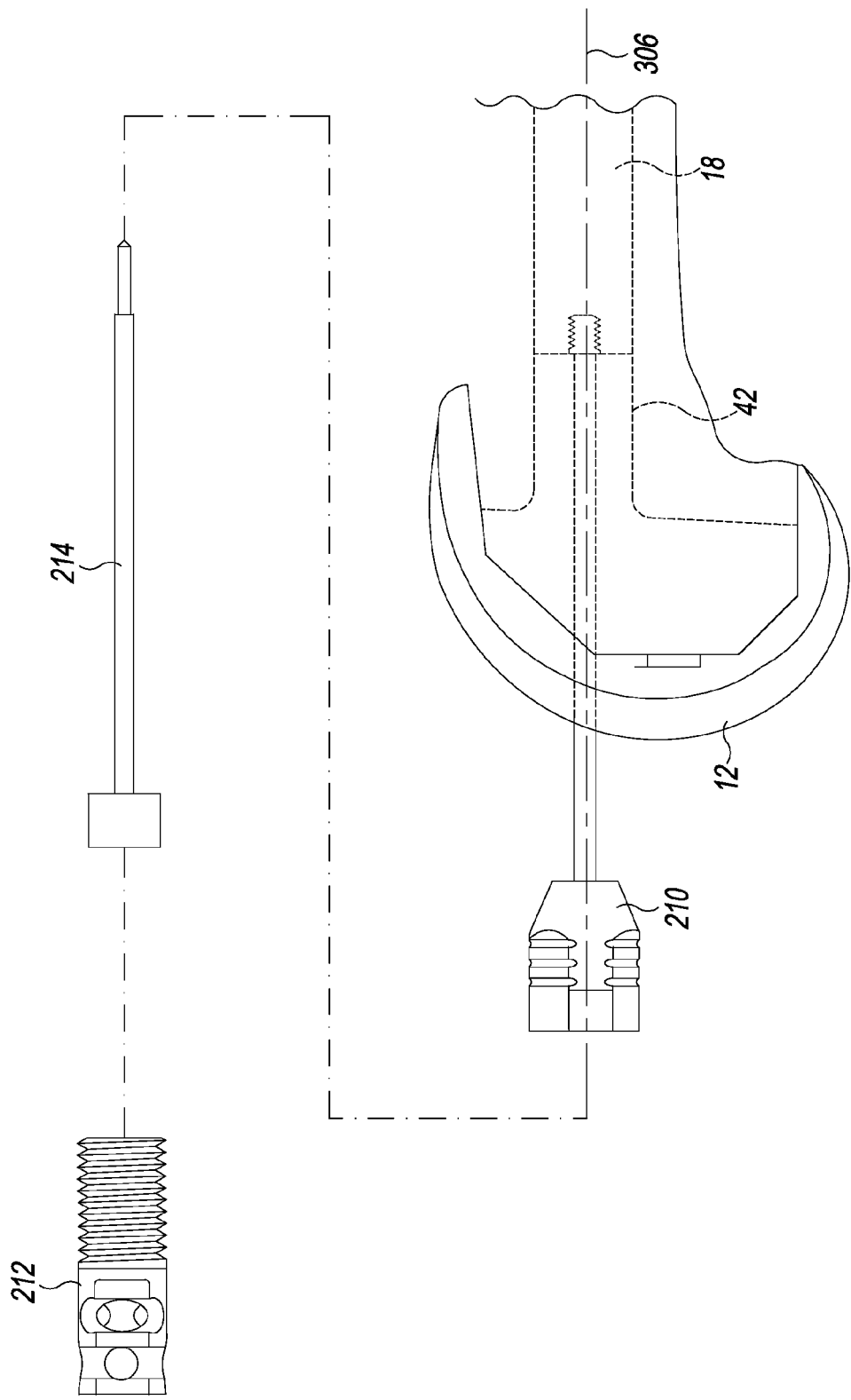

Further, as shown in FIG. 11, the surgeon removes the retention device 74 using any suitable means. For example, in one embodiment, a screw (e.g., a cork screw) may be driven into the bore 138 of the retention device 74, and the retention device 74 may be removed by force along the axis 306. Depending on the particular retention device 74 used, another method of removal may be used. For example, in some embodiments, a removal tool (not shown) may permit nearly effortless removal of the retention device 74. Referring now to FIG. 12, the disassembly tool 208 may be assembled as attached to the femoral component 12. To do so, the main component 210 of the disassembly tool 208 is secured to the femoral component 12. For example, in the illustrative embodiment, the elongated body 224 of the main component 210 may be threaded into the threaded passage 92 of the femoral component 12.

The rod component 214 is then selected for use with the femoral component assembly 72. As described herein, the head 258 of the rod component 214 is configured to engage the aperture 264 defined in the inferior end 266 of the spindle component 212, and the inferior end 274 of the elongated shaft 260 of the rod component 214 is configured to engage and apply a force against the engagement surface 217 of the stem component 18. Therefore, the length 270 of the elongated shaft 260 of the rod component 214 must correspond with the particular orthopaedic prosthetic assembly 10 being disassembled. Specifically, because the length of the elongated body 224 of the main component 210 is static, the suitable length 270 of the rod component 214 is a function of the distance between (i) a threaded passageway to which the elongated body 224 of the main component 210 is to thread and (ii) the engagement surface 217 with which the rod component 214 is to engage. Accordingly, it should be appreciated that the rod component 214 chosen to remove a particular orthopaedic prosthetic component from the assembly 10 may be chosen from a collection 318 of rod components 214, each having a shaft 260 with a different length 270 suited to the removal of a particular prosthetic component.

As such, in the illustrative embodiment, the rod component 214 is selected with a length 270 corresponding to a femoral component assembly 72 including only a femoral component 12 and a stem component 18. After making the appropriate selection, the elongated shaft 260 of the rod component 214 is inserted through the aperture 226 defined in the housing 222 and through the bore 244 in the elongated body 224 of the main component 210. After inserting the rod component 214 through the elongated body 224, the threaded body 282 of the spindle component 212 is threaded into the main component 210.

Figure 13:
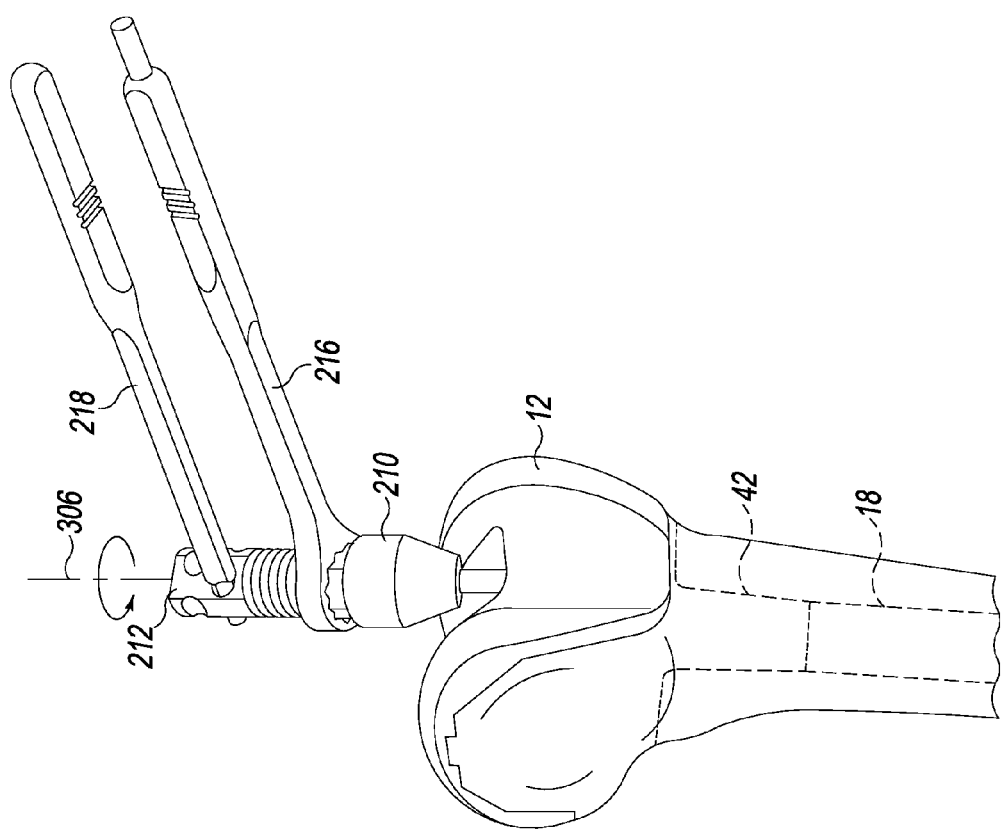
Figure 14:
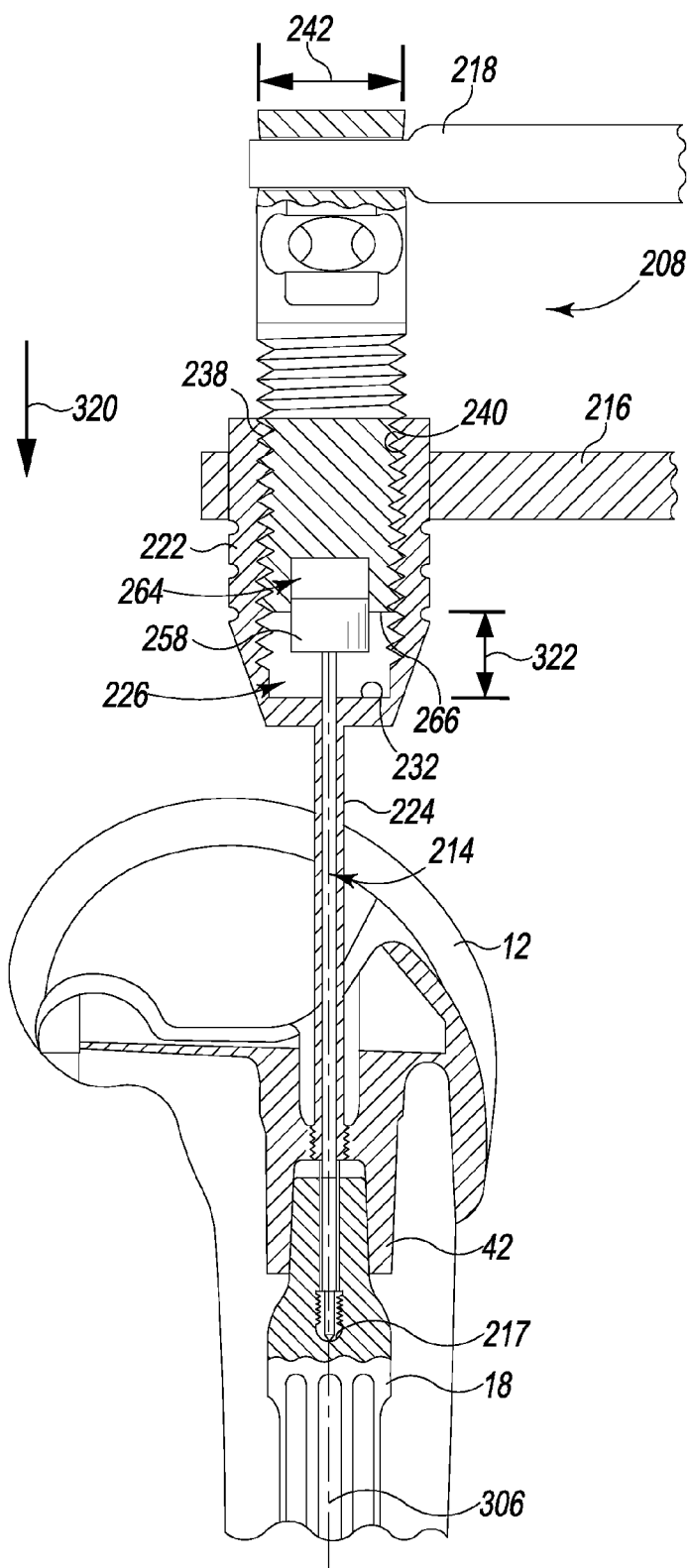
Figure 15:
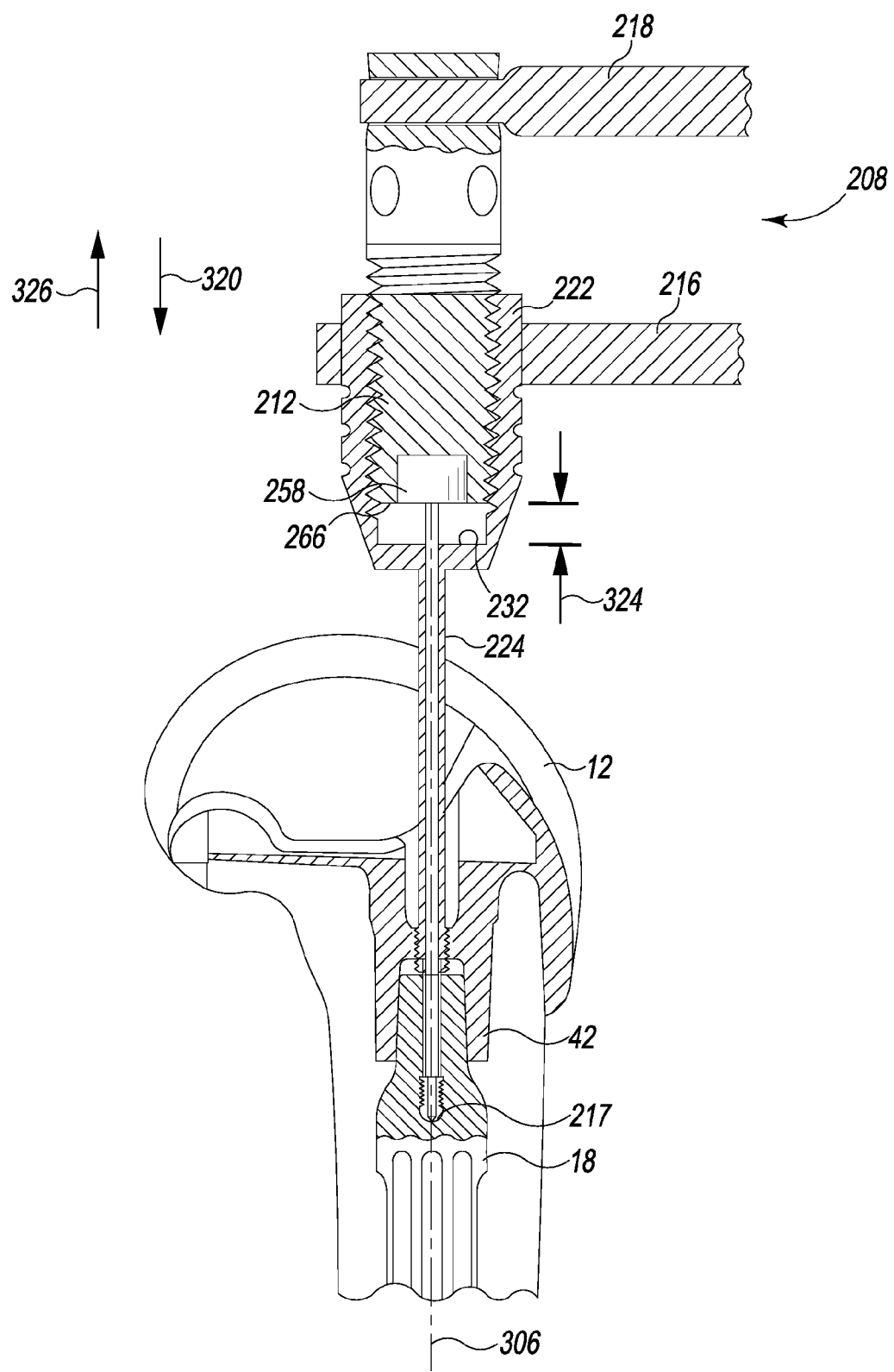

As shown in FIGS. 13-15, the surgeon secures the wrench component 216 and the handle component 218 to the main component 210 and the spindle component 212 of the disassembly tool 208, respectively. After securing those components 210, 212, the surgeon may steady the disassembly tool 208 and prevent the disassembly tool 208 from unthreading from a first orthopaedic prosthetic component (e.g., the femoral component 12) with the wrench component 216 while rotating the handle component 218 relative to the wrench component 216 to further thread the spindle component 212 into the main component 210. Doing so increases a force applied to the rod component 214 and, therefore, to the engagement surface of a second prosthetic component (e.g., the engagement surface 217 of the stem component 18). At some point, the force applied to the engagement surface (e.g., the engagement surface 217) may exceed a threshold force (e.g., a breakaway force) required to break a taper fit between the first prosthetic component (e.g., the femoral component 12) and the second prosthetic component (e.g., the stem component 18). Accordingly, those prosthetic components may disengage once the threshold force is reached.

Referring now to FIG. 14, the spindle component 212 has been threaded into the housing 222 of the main component 210 such that a distance 322 between the inferior end 266 of the spindle component 212 and the annular surface 232 of the housing 222 is defined. As shown in FIG. 15, after the spindle component 212 has been further threaded into the main component 210 in a first direction 320, a different distance 324 between the inferior end 266 of the spindle component 212 and the annular surface 232 of the housing 222 is defined, which is a shorter distance 324 than the distance 322. It should be appreciated that as the spindle component 212 is further threaded into the main component 210 in the first direction 320, the distance between the inferior end 266 of the spindle component 212 and the annular surface 232 of the housing 222 of the main component 210 decreases.

As discussed above, continuing to thread the spindle component 212 into the main component 210 in the first direction 320 increases the force applied to the rod component 214 along the longitudinal axis 306. Accordingly, the force applied to the attached stem component 18 increases. The femoral component 12 breaks loose when the force applied to the stem component 18 reaches the threshold force required to break the taper fit between the femoral component 12 and the stem component 18. That is, the femoral component 12 is moved in a second direction 326 opposite the first direction 320 relative to the stem component 18. Once the femoral component 12 has been broken free and removed, the stem component 18 may be removed from the patient using any suitable means (e.g., traditional means). For example, a screw may be threaded into the threaded section 114 of the aperture 112 of the stem component 18 and a "slap hammer" or other surgical instrument may be used to drive or force the stem component 18 from the patient's femur.

As discussed above, in some embodiments a femoral sleeve component 56 is used in conjunction with a stem component 18 to facilitate implantation of the femoral component 12 in the presence of reduced bone quality in the patient's femur (e.g., the femoral component assembly 72 of FIGS. 6-7). In such an embodiment, the disassembly tool 208 (with the appropriate rod component 214) may be assembled and secured to the threaded passage 92 of the femoral component 12. As discussed above, the inferior end 274 of the elongated shaft 260 of the rod component 214 (i.e., the end 274 configured to protrude from the elongated body 224 of the disassembly tool 208) may be shaped to fit or otherwise contact the driver aperture 128 defined in the head 118 of the fastener 76. As such, a force is applied to the head 118 of the fastener 76 as the spindle component 212 is threaded into the main component 210 of the disassembly tool 208 rather than the force being applied directly to the stem component 18.

Once the femoral component 12 breaks loose from the femoral sleeve component 56, the femoral component 12 may be removed from the assembly (e.g., using a slap hammer). Thereafter, the fastener 76 and the retention device 74 may be removed from the femoral sleeve component 56 and stem component 18 as described above. After the fastener 76 and retention device 74 are removed, the disassembly tool 208 (with an appropriate rod component 214) may be secured to the threaded passage 178 of the femoral sleeve component 56. It should be appreciated that the rod component 214 used for removing the femoral component 12 may have a different length 270 than the rod component 214 used to remove the femoral sleeve component 56. The femoral sleeve component 56 is loosened from the stem component 18 using the disassembly tool 208 and the methods described herein. Additionally, the femoral sleeve component 56 and the stem component 18 may be removed thereafter using suitable means (e.g., using a slap hammer).

Figure 16:
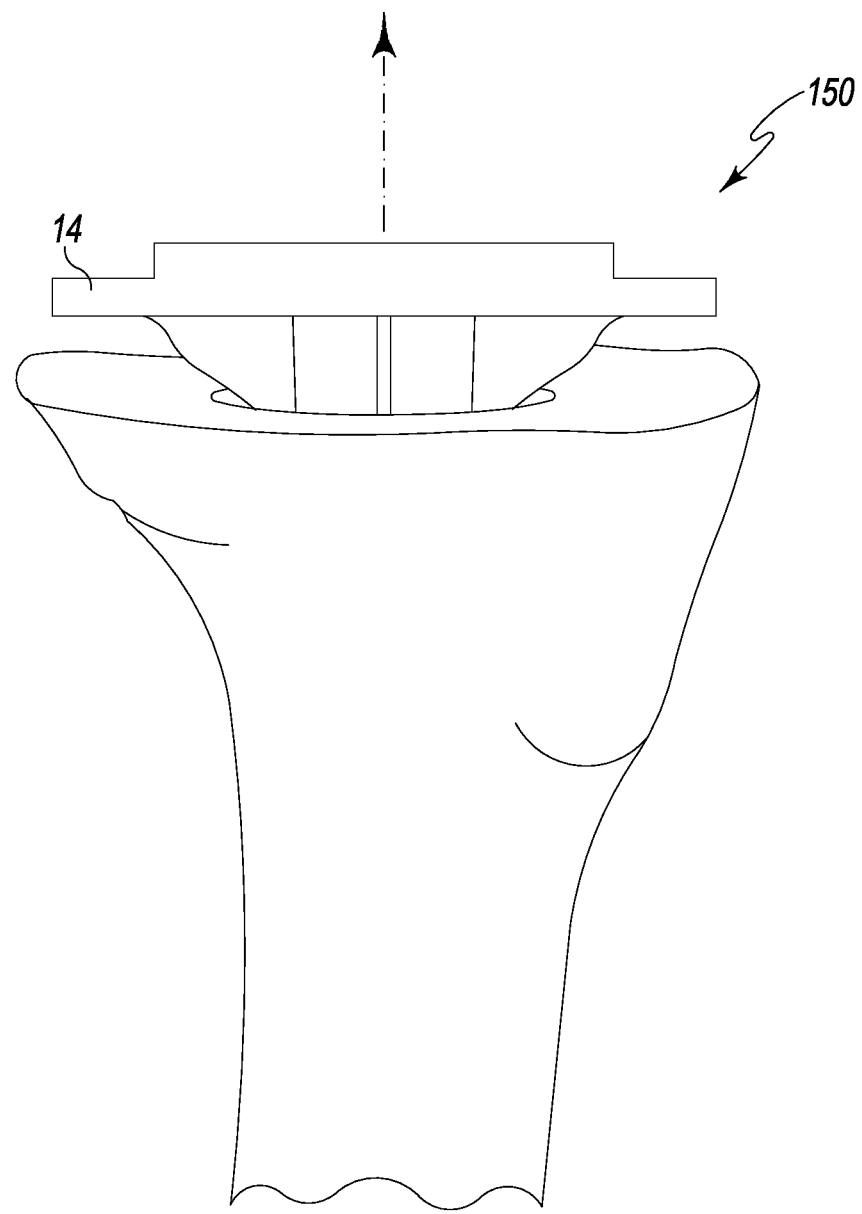
FIGS. 16-18 show the disassembly tool of FIG. 9 used in an orthopaedic surgical procedure with the tibial component assembly of FIG. 8.
Figure 17:
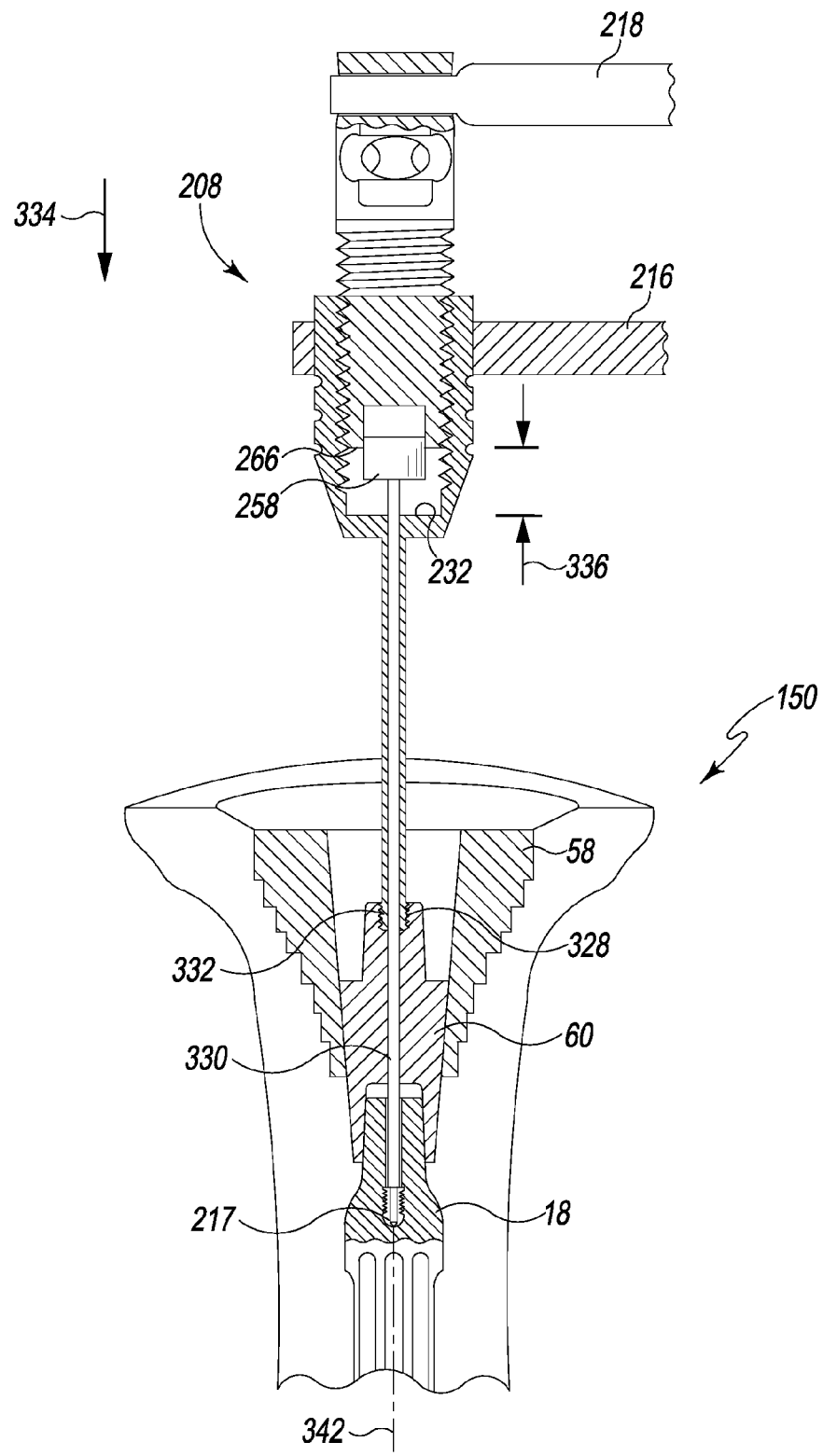
Figure 18:
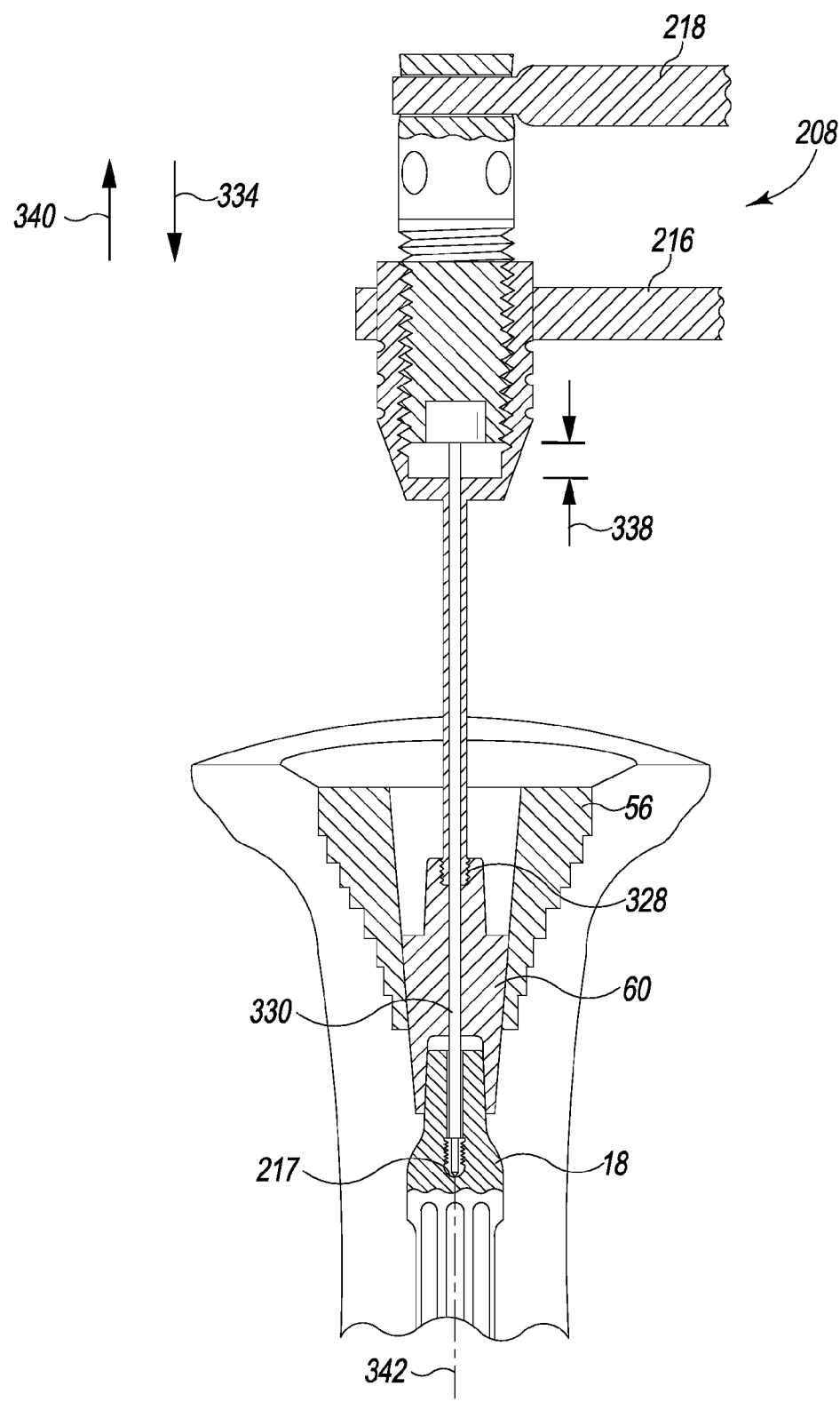

As shown in FIGS. 16-18, disassembly of a tibial component assembly 150 includes the use of the disassembly tool 208. The tibial component assembly 150 shown in FIGS. 16-18 includes the tibial tray 14, the stem component 18, the tibial sleeve component 58, the stem adaptor 60, and optionally the fastener 76. As shown in FIG. 16, the tibial tray 14 may be removed from the tibial component assembly 150 using any suitable means (e.g., traditional means). Accordingly, if the fastener 76 is used, it may be removed in addition to the tibial tray 14 as discussed above. After removing the tibial tray 14, the tibial sleeve component 58, the stem adaptor 60, and the stem component 18 of the tibial component assembly 150 remain assembled.

As shown in FIGS. 17-18, the disassembly tool 208 is assembled and secured to the threaded passage 328 of the stem adaptor 60. Specifically, the elongated body 224 of the main component 210 is threaded into the threaded passage 328 of the stem adaptor 60. Additionally, a rod component 214 is chosen with a length 270 corresponding to a tibial component assembly 150 including only the stem adaptor 60 and the stem component 18 and advanced through the bore 244 of the elongated body 224 to engage the engagement surface 217 of the stem component 18. Thereafter, the surgeon threads the spindle component 212 into the main component 210 of the disassembly tool and secures the wrench component 216 and the handle component 218.

Referring now to FIG. 17, the spindle component 212 has been threaded into the housing 222 of the main component 210 such that a distance 336 between the inferior end 266 of the spindle component 212 and the annular surface 232 of the housing 222 is defined. As shown in FIG. 18, after the spindle component 212 has been further threaded into the main component 210 in a first direction 334, a different distance 338 between the inferior end 266 of the spindle component 212 and the annular surface 232 of the housing 222 is defined, which is a shorter distance 338 than the distance 336. As described above in reference to FIGS. 14-15, as the spindle component 212 is further threaded into the main component 210, the distance between the inferior end 266 of the spindle component 212 and the annular surface 232 of the housing 222 of the main component 210 decreases, and the force applied to the rod component 214 (and therefore to the stem component 18) along a longitudinal axis 342 increases.

The stem adaptor 60 breaks loose when the force applied to the stem component 18 reaches the threshold force required to break the taper fit between the stem adaptor 60 and the stem component 18. That is, the stem adaptor 60 is moved in a second direction 340 opposite the first direction 334 relative to the stem component 18. Once the stem adaptor 60 has been broken free and removed, the stem component 18 and the tibial sleeve component 58 may be remove from the patient using any suitable means (e.g., traditional means). For example, a screw may be threaded into the threaded aperture 110 of the stem component 18 and a "slap hammer" or other surgical instrument may be used to drive or force the stem component 18 from the patient's tibia. In some cases, the force associated with extracting the stem component 18 loosens the tibial sleeve component 58 as well.

As discussed above, in some embodiments a tibial component assembly 150 includes only the tibial tray 14, the stem component 18, and the fastener 76. The methods described herein may also be used to disassemble such an assembly. Specifically, the fastener 76 may be removed using, for example, the driver 308 as described above. After a rod component 214 having a suitable length for the assembly 150 is chosen, the disassembly tool 208 is secured to the threaded passage 166 of the tibial tray 14, assembled, and operated as discussed above to loosen the tibial tray 14 from the stem component 18. The stem component 18 may then be removed (e.g., using a slap hammer or other removal tool).

Figure 19:
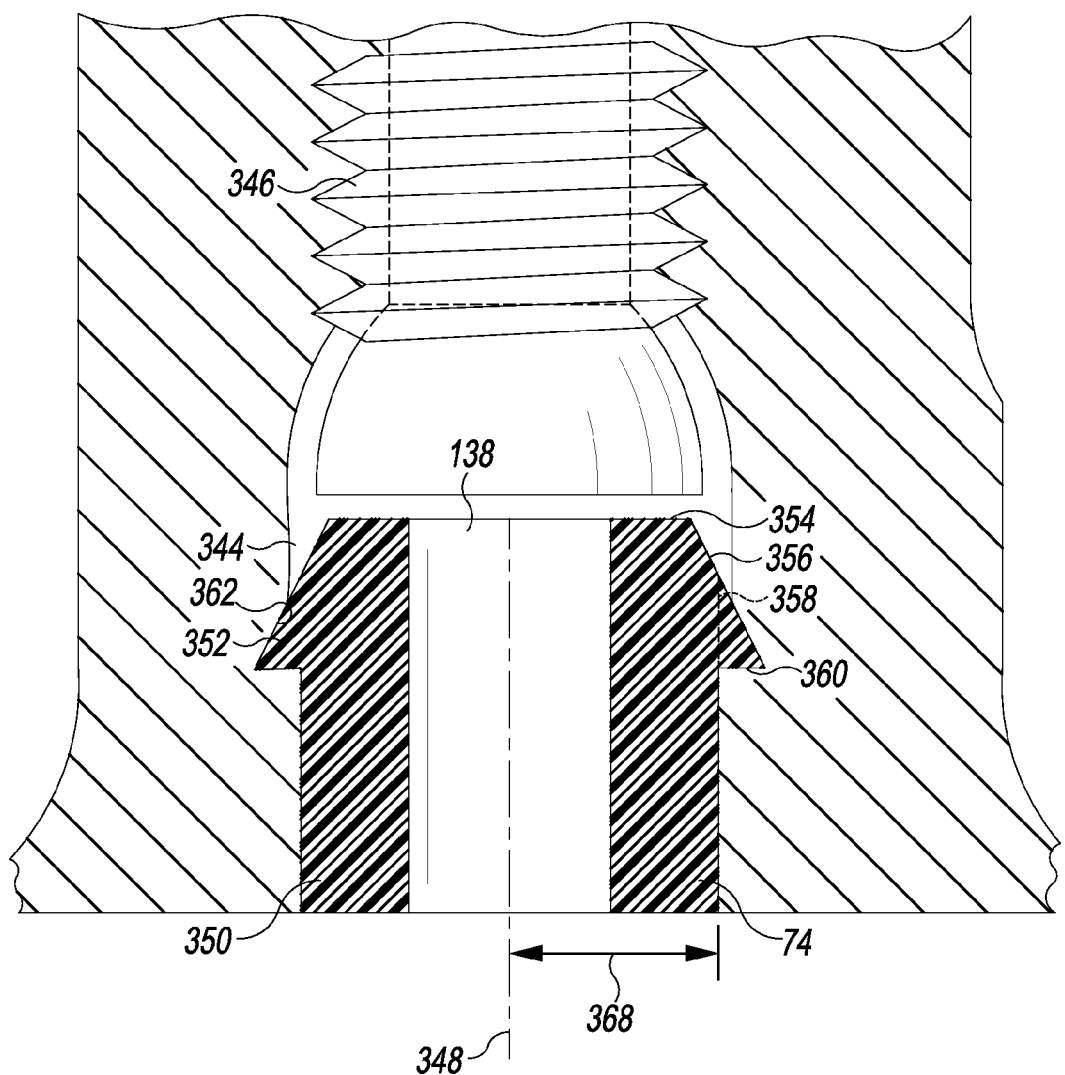
FIG. 19 shows a cross sectional view of another embodiment of the retention device.
Figure 20:
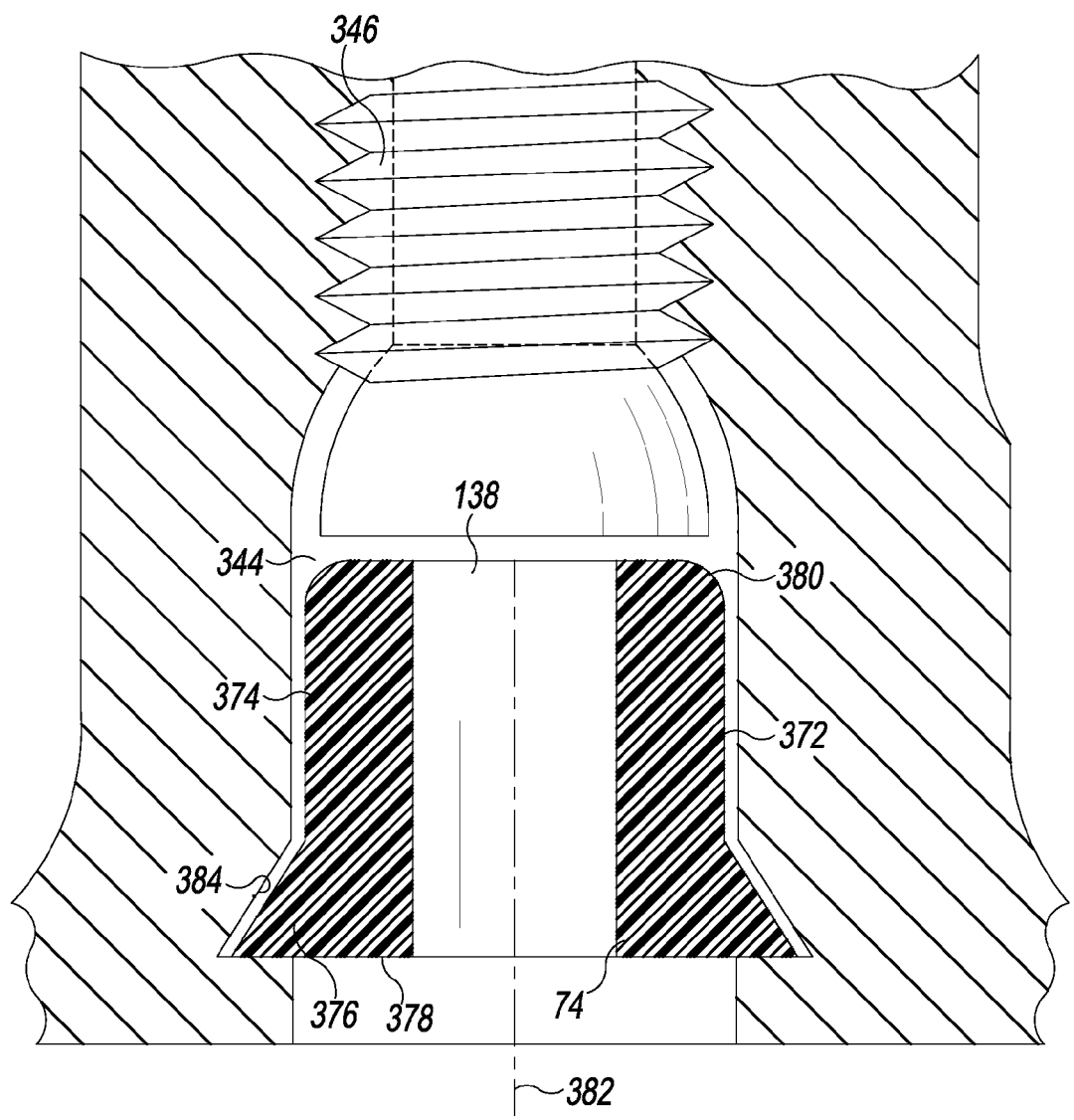
FIG. 20 shows a cross sectional view of another embodiment of the retention device.
Figure 21:
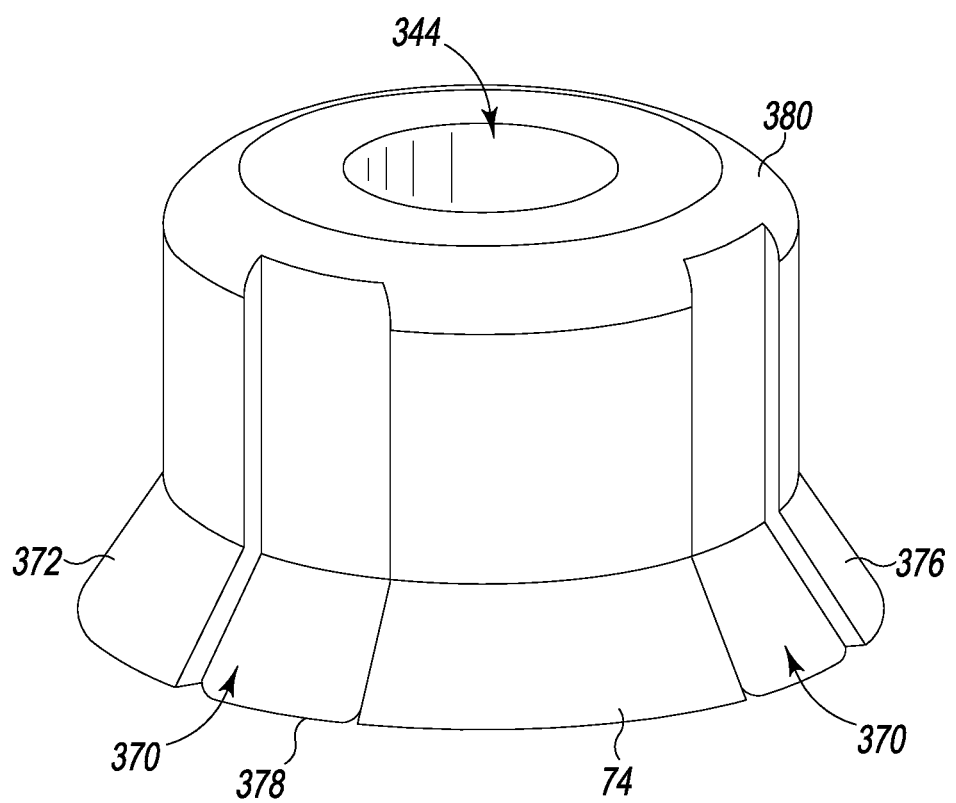
FIG. 21 shows a perspective view of the retention device of FIG. 20.

Referring now to FIGS. 19-21, as discussed above, other retention devices 74 may be used in other embodiments to secure the fastener 76 (i.e., prevent the fastener 76 from "backing out"). Depending on the embodiment, use of other retention devices 74 may require minor modification to one or more components of the orthopaedic prosthetic assemblies 10 described above (e.g., to the distal compartment 90 of the femoral component 12).

As shown in FIG. 19, the retention device 74 may be mushroom-shaped and configured to fit in a passageway 344 outside a threaded passage 346. In the case of retaining a femoral component 12 to a stem component 18, the retention device 74 may be configured to rest in the distal compartment 90 of the stem post 42 of the femoral component 12. The mushroom shaped retention device 74 has radial symmetry about an axis 348. Specifically, the retention device 74 includes an annular cylinder 350 with a radially extending frustoconical body 352 extending from the annular cylinder 350 at a proximal end 354 of the retention device 74. That is, a cross section taken along the radial axis 348 of the retention device 74 shows a triangular section 356 at the proximal end 354 of the retention device 74 with one base 358 of the triangle 356 being coincident with the annular cylinder 350 and the other base 360 perpendicular to the annular cylinder 350 and offset from the proximal end 354 of the retention device 74 by the length of the base 358.

Accordingly, in an embodiment using such a retention device 74, the passageway 344 may include a groove 362 sized to fit the frustoconical body 352 of the retention device 74 in such a way as to hold the retention device 74 in place. In some embodiments, a bore 138 defined through the axis 348 of the retention device 74 may be used, for example, by a removal tool (not shown) to remove the retention device 74. It should be appreciated that the retention device 74 is similar to the retention device 74 discussed above with regard to FIGS. 2-3 but is inserted into the passageway 344 in an opposite direction and not placed in the threaded passage 346. Accordingly, during disassembly, the retention device 74 may be removed prior to removing the fastener 76, thereby affording join line access to the fastener 76. Additionally, the retention device 74 of FIG. 19 may have a larger radius 368 than that of the retention device 74 discussed above vis-à-vis FIGS. 2-3.

As shown in FIG. 20-21, another retention device 74 may be used to secure the fastener 76 and may similarly be configured to rest in the passageway 344. As shown, the retention device 74 is generally radially symmetric about an axis 382 and includes an annular cylinder 374 with a frustoconical body 376 extending from a distal end 378 of the retention device 74 and grooves 370 along the outer surface 372 of the retention device 74 for use by a removal tool (not shown). Additionally, in some embodiments, the proximal end 380 of the retention device 74 may be rounded. As in the case of the retention device 74 of FIG. 19, in an embodiment using such a retention device 74, the passageway 344 may include a groove 384 sized to fit the frustoconical body 376 of the retention device 74 in such a way as to hold the retention device 74 in place.

In other embodiments, another retention device 74 may be used to secure the fastener 76 within the passageway 344 or the threaded passage 346. For example, in some embodiments, the passageway 344 defines a groove into which a retention device 74 may be inserted, similar to the groove 384 discussed above. The groove may be shaped to fit, for example, an o-ring sized to prevent the fastener 74 from moving beyond the groove. In some embodiments, the o-ring may be helical, whereas in other embodiments, the o-ring may be a substantially annular body or an annular cylinder. In yet another embodiment, the retention device 74 may include a c-clip shaped to fit into the groove. Alternatively, the retention device 74 may include a bore through which the fastener 76 is inserted, and the retention device 74 may be received in the threaded passage 346 rather than in the passageway 344. For example, the retention device 74 may include or otherwise constitute a countersunk washer, an external tooth washer, an external tooth serrated washer, or an angled washer configured to be received in the threaded passage 346.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic surgical instrument comprising:
   a main component including a housing and an elongated body extending from the housing, the housing and the elongated body defining a longitudinal axis, wherein a passageway is defined in the elongated body along the longitudinal axis,
   a rod component including (i) a head configured to be received in the housing of the main component and (ii) an elongated shaft extending from the head, configured to pass through the elongated body of the main component, and
   a spindle component including (i) a threaded body configured to engage the head of the rod component to move the rod component along the longitudinal axis as the threaded body is threaded into the housing, and (ii) a handle body opposite the threaded body,
   wherein the elongated shaft has a length greater than a length of the elongated body of the main component,
   wherein the head of the rod component has a diameter greater than a diameter of the passageway of the elongated body of the main component, and
   wherein the handle body is configured to receive a handle component for threading the spindle component.

2. The orthopaedic surgical instrument of claim 1, wherein the rod component is selected from a plurality of rod components, each rod component of the plurality of rod components having an elongated shaft with a different length.

3. The orthopaedic surgical instrument of claim 1, wherein an end of the elongated body of the main component opposite the housing has a threaded outer surface.

4. The orthopaedic surgical instrument of claim 1, wherein the spindle component includes an aperture defined at an end of the threaded body, the aperture sized to fit the head of the rod component.

5. The orthopaedic surgical instrument of claim 4, wherein a diameter of the aperture is less than a diameter of the spindle component.

6. The orthopaedic surgical instrument of claim 1, wherein an outer surface of the housing of the main component is shaped to match a connection surface of a wrench component.

7. The orthopaedic surgical instrument of claim 6, wherein the outer surface is shaped to match a connection surface of a hex wrench.

* * * * *